(12) United States Patent
Segermark et al.

(10) Patent No.: US 6,746,396 B1
(45) Date of Patent: Jun. 8, 2004

(54) SELF-SEATING SURGICAL ACCESS DEVICE AND METHOD OF USE

(75) Inventors: James D. Segermark, Gem Lake, MN (US); Christopher J. Herman, White Bear Lake, MN (US)

(73) Assignee: ViaMedics, LLC, White Bear Lake, MN (US)

( * ) Notice: Subject to any disclaimer, the term of this patent is extended or adjusted under 35 U.S.C. 154(b) by 0 days.

(21) Appl. No.: 09/647,887

(22) PCT Filed: Apr. 13, 1999

(86) PCT No.: PCT/US99/08021

§ 371 (c)(1),
(2), (4) Date: Oct. 5, 2000

(87) PCT Pub. No.: WO99/52448

PCT Pub. Date: Oct. 21, 1999

(51) Int. Cl.⁷ .................................................. A61B 1/32
(52) U.S. Cl. ........................ 600/233; 600/219; 600/231
(58) Field of Search ................................ 600/201, 208, 600/217, 219, 225, 231, 232, 233, 227; 128/850, 852

(56) References Cited

U.S. PATENT DOCUMENTS

| 475,975 | A | 5/1892 | Clough |
| 1,157,202 | A | 10/1915 | Bates et al. |
| 1,707,689 | A | 4/1929 | Sloan |
| 1,963,173 | A | 6/1934 | Morin |
| 2,697,433 | A | 12/1954 | Zehnder ........................ 128/83 |
| 2,812,758 | A | 11/1957 | Blumenschein |
| 3,016,899 | A | 1/1962 | Stenvall |
| 3,017,887 | A | 1/1962 | Heyer |
| 3,021,842 | A | 2/1962 | Flood |
| 3,038,468 | A | 6/1962 | Raeuchle |
| 3,656,485 | A | 4/1972 | Robertson |
| 3,807,393 | A | 4/1974 | McDonald |
| 3,863,639 | A | 2/1975 | Kleaveland |
| 3,893,454 | A | 7/1975 | Hagelin |
| 4,112,934 | A | 9/1978 | Rizk |
| 4,492,229 | A | 1/1985 | Grunwald |
| 4,726,356 | A | 2/1988 | Santilli et al. |
| 4,765,311 | A | 8/1988 | Kulik et al. |
| 4,924,857 | A | * 5/1990 | Mahmoodian |
| 4,955,891 | A | 9/1990 | Carol .......................... 606/130 |
| 4,971,037 | A | 11/1990 | Pelta |
| 4,998,938 | A | 3/1991 | Ghajar et al. ............... 606/130 |
| D319,502 | S | 8/1991 | Michelson ................. D24/135 |
| 5,088,472 | A | 2/1992 | Fakhrai |
| 5,125,396 | A | 6/1992 | Ray |

(List continued on next page.)

FOREIGN PATENT DOCUMENTS

| DE | 40 28 651 | 3/1992 | ........... A61B/17/02 |
| EP | 0 792 620 A2 | 9/1997 | ........... A61B/17/02 |
| EP | 0 792 620 A3 | 1/1998 | ........... A61B/17/02 |
| WO | WO 96/02195 | 2/1996 | ........... A61B/17/02 |
| WO | WO 98/12960 | 4/1998 | ............ A61B/1/22 |

OTHER PUBLICATIONS

Promotional literature for Cardio Thoracic Systems, published on the Internet at least as early as Feb. 1998.

*Primary Examiner*—Jeffrey A. Smith
(74) *Attorney, Agent, or Firm*—Sherrill Law Offices, PLLC

(57) ABSTRACT

A surgical access device includes two opposed side members each of which carries a downwardly depending flange. One lateral member adjustably connects a first end of the first side member to a first end of the second side member, with at least one of these first ends being moveable along a length of the first lateral member, thereby permitting adjustment of the space between the first ends. A second lateral member adjustably connects the second end of the first side member to the second end of the second side member, with at least one of these second ends being moveable along a length of the second lateral member, thereby permitting adjustment of the space between the second ends.

21 Claims, 26 Drawing Sheets

U.S. PATENT DOCUMENTS

| | | |
|---|---|---|
| 5,150,706 A | 9/1992 | Cox et al. |
| 5,201,742 A | 4/1993 | Hasson .................. 606/130 |
| 5,299,563 A * | 4/1994 | Seton |
| 5,375,588 A | 12/1994 | Yoon |
| 5,391,156 A | 2/1995 | Hildwein et al. ........... 604/174 |
| 5,425,357 A | 6/1995 | Moll et al. |
| 5,460,170 A | 10/1995 | Hammerslag ............... 600/201 |
| 5,505,690 A | 4/1996 | Patton et al. ............... 600/210 |
| 5,512,038 A | 4/1996 | O'Neal et al. .............. 600/210 |
| 5,514,076 A | 5/1996 | Ley ........................... 600/206 |
| 5,520,610 A * | 5/1996 | Giglio et al. ............... 600/233 |
| 5,522,791 A | 6/1996 | Leyva ........................ 600/207 |
| 5,540,648 A | 7/1996 | Yoon ......................... 600/114 |
| 5,613,937 A | 3/1997 | Garrison et al. ............ 600/201 |
| 5,616,117 A | 4/1997 | Dinkler et al. .............. 600/232 |
| D381,746 S | 7/1997 | Koros et al. ................ D24/133 |
| 5,658,272 A | 8/1997 | Hasson ......................... 606/1 |
| 5,688,223 A | 11/1997 | Rosendahl ................... 600/215 |
| 5,776,054 A | 7/1998 | Bobra ........................ 600/219 |
| 5,779,629 A * | 7/1998 | Hohlen ....................... 600/219 |
| 5,788,630 A | 8/1998 | Furnish ...................... 600/232 |
| D397,791 S | 9/1998 | Koros et al. ................ D24/135 |
| D403,066 S | 12/1998 | DeFonzo .................... D24/135 |
| 5,865,731 A | 2/1999 | Lenox et al. ............... 600/232 |
| D411,617 S | 6/1999 | Furnish ...................... D24/135 |
| 5,931,778 A | 8/1999 | Furnish ...................... 600/232 |
| 5,951,466 A | 9/1999 | Segermark et al. ......... 600/225 |
| 6,224,545 B1 * | 5/2001 | Cocchia et al. ............. 600/233 |

* cited by examiner

SELF-SEATING SURGICAL ACCESS DEVICE AND METHOD OF USE

This patent claims priority as a national-phase application of PCT patent application No. PCT/US99/08021 (Int' Filing Date Apr. 13, 1999; WIPO Int'l Publ. No. (U.S. Pat. No. 6,488,620); Int'l Publ. Date Oct. 21, 1999 (in Engligh)), which, in turn, claims priority as a continuation-in-part to U.S. patent application Ser. No. 09/059,693 (filed Apr. 13, 1998) (U.S. Pat. No. 5,951,466).

FIELD OF THE INVENTION

The present invention provides an improved surgical access device of the type, which is used to gain access to an internal cavity of a patient's body. A preferred embodiment of the invention is useful both as an access port and as a tissue retractor.

BACKGROUND OF THE INVENTION

Surgeons frequently need to gain access to patients' body cavities to perform various procedures. One way to gain access to such a cavity is to perform invasive surgery where the cavity is opened fairly widely from the exterior to allow the surgeon ready access to the interior of the cavity. For example, in most traditional heart surgery, the patient's sternum is split and the overlying tissue is cut back to allow the surgeon to place both hands inside the chest cavity.

Increasingly, however, less invasive techniques are being employed to permit access to body cavities. For example, endoscopic examinations are being used to explore body cavities without having to directly visually inspect them. Gall bladder surgery is also being done increasingly by gaining access to the abdominal cavity through smaller access ports through the abdominal wall rather than using more invasive approaches. (See, for example, U.S. Pat. No. 5,375,588, issued to Yoon, the teachings of which are incorporated herein by reference.)

Increasingly, surgeons are gaining access to the thoracic cavity by passing surgical instruments into the cavity through the intercostal spaces between a patient's ribs. For example, U.S. Pat. No. 5,613,937 (Garrison et al., the teachings of which are incorporated herein by reference) suggests a method of conducting closed-chest heart surgery by passing surgical implements through a number of ports positioned in the intercostal spaces. This patent shows one access cannula which provides an oblong opening which allows a surgeon to pass a replacement valve into the thoracic cavity for placement in the patient's heart.

A wide variety of surgical retractors are also known in the art. Most surgical retractors are intended to allow a surgeon to forcibly urge tissue out of the way to enable unfettered access to the underlying anatomical structures. For example, U.S. Pat. No. 4,765,311 (Kulik et al., the teachings of which are incorporated herein by reference), shows a "wound retractor" which comprises a split tube. Each of the two tube halves are carried on holders which can be moved apart from one another to retract the tissue and provide access to the abdominal cavity. U.S. Pat. No. 1,157,202 (Bates) teaches a retractor which is used to retract the sides of an incision in the abdominal wall. This retractor includes four separate retractile elements, which are arranged about an oval frame. The tissue can be pulled apart to expand the size of the opening of the incision by pulling the retractile elements away from one another.

U.S. Pat. No. 5,125,396 (Ray, the teachings of which are incorporated herein by reference), suggests a surgical retractor which comprises two separate arcuate blades. A separate ring carries each of these arcuate blades. By turning these two rings with respect to one another, one can move the blades with respect to one another to open a generally cylindrical passageway through the patient's tissue.

SUMMARY OF THE INVENTION

The present invention contemplates both a surgical access device and a method of gaining surgical access to a body cavity. In accordance with one embodiment of the invention, a surgical device for accessing the body cavity includes first and second opposed side members. Each of the side members has first and second ends and carries a downwardly depending flange. A first lateral member adjustably connects the first end of the first side member to the first end of the second side member. At least one of the first ends is movable along a length of the first lateral member, thereby permitting adjustment of the space between the first ends of the side members. A second lateral member adjustably connects the second end of the first side member to the second side of the second side member. At least one of the second ends is movable along a length of the second lateral member, thereby permitting adjustment of the space between the second ends of the side members. If so desired, the surgical device may have an insertion configuration wherein the flange carried by the first side member abuts the flange carried by the second side member to define a leading edge of the device which can be inserted into a single, elongated incision.

An alternative surgical device of the invention includes a frame having separable first and second side members. This frame has an insertion configuration and at least one retracting configuration. At least one flange is carried by the first side member. This flange is movable between an insertion position and at least one retracting position. At least one flange is carried by the second side member. This flange is also movable between an insertion position and at least one retracting position. The surgical device also includes at least one actuator having first and second lateral segments. The first lateral segment is carried by the first side member and has a control surface adapted to engage a deployment surface of the flange of the first side member. The second lateral segment is carried by the second side member and has a control surface adapted to engage a deployment surface of the flange of the second side member. The first and second lateral segments of the actuator are positioned adjacent to one another when the frame is in its insertion configuration, permitting the lateral segments to be urged downwardly together as a unit for simultaneous deployment of the flanges. When the frame is in its retracting configuration, though, the first and second lateral segments of the actuator are spaced from one another. In a further refinement of this embodiment, the actuator has an insertion position and at least one retracting position. The flanges are movable into their respective insertion positions when the actuator is in its insertion position. When the actuator is in one of its retracting positions, though, it will bias each flange into a respective retracting position.

The invention also contemplates a method of gaining surgical access to a body cavity. In accordance with this method, one is provided with a surgical implant comprising a frame having first and second opposed side members. Each of the side members has first and second ends and carries a downwardly depending flange. A first lateral member adjustably connects the first end of the first side member to the first end of the second side member. A second lateral member adjustably connects the second end of the first side member to the second end of the second side member. An incision is made to the patient's tissue to define an opening therethrough. The flanges of the first and second side members are simultaneously inserted through the incision. Thereafter, the first and second flanges are urged laterally away from one another, thereby simultaneously expanding the opening through the patient's tissue and centering the access port laterally within the opening. At least one of the first end of the first side member and the first end of the second side member is moved along a length of the first lateral member. This moves the first ends of the two side members away from one another and may also expand and reshape the opening. In one particularly preferred embodiment, the method further includes the step of moving at least one of the second ends of the first and second sides along a length of the second lateral member to move the second ends of the side members away from one another.

DETAILED DESCRIPTION OF THE PREFERRED EMBODIMENTS

Figure 1:
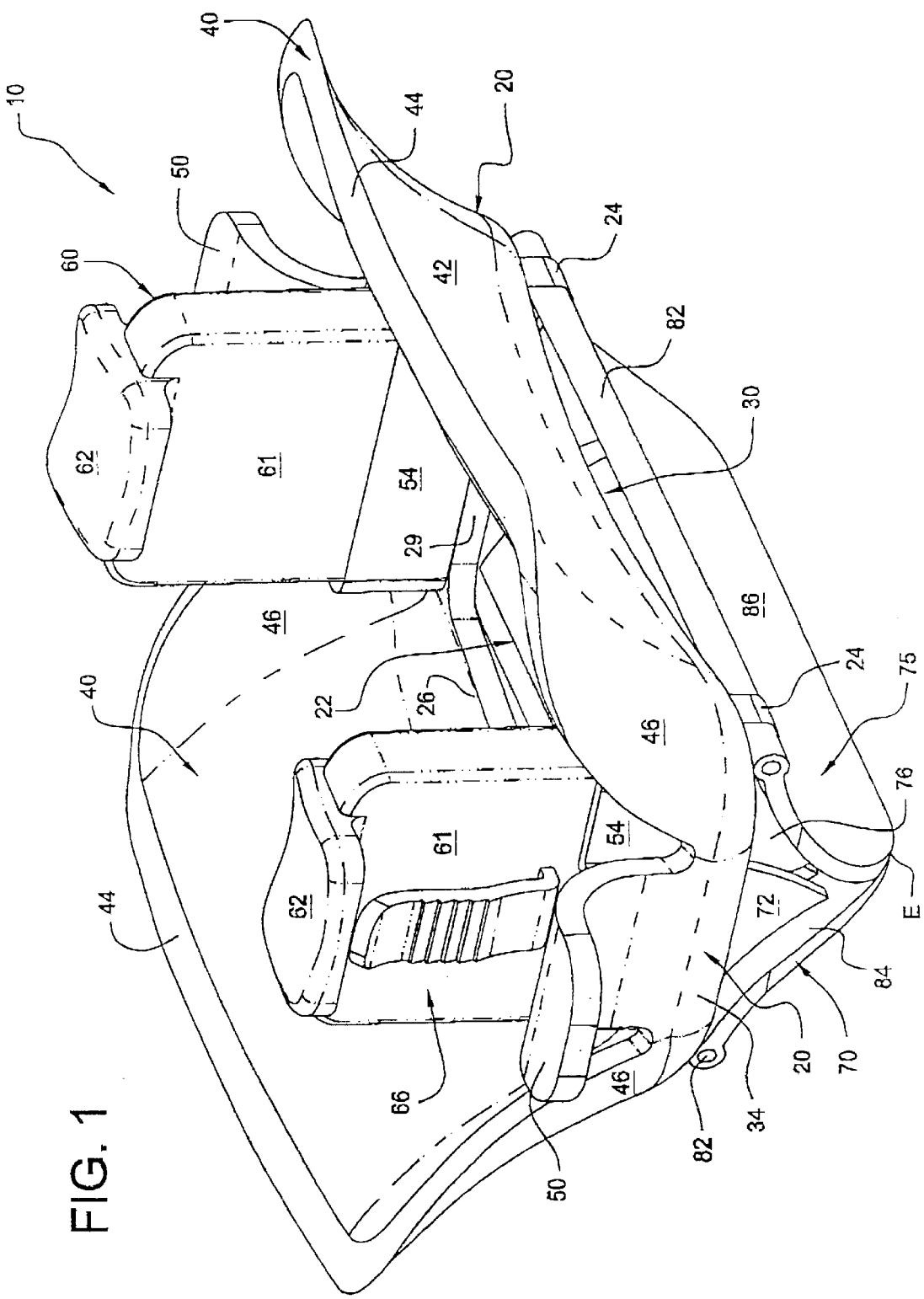
FIG. 1 is a top perspective view of a surgical access device in accordance with one embodiment of the present invention.

Nomenclature
10 Device
20 Frame
22 Access port
24 Hinge Fitting
26 First Longitudinal Side of Access port
27 Second Longitudinal Side of Access port
28 First End of Frame
29 Second End of Frame
30 Lower Surface of Frame
32 Upper Surface of Frame
40 Wing
42 Outer Surface of Wing
44 Upper Edge of Wing
46 Curved Side of Wing
50 Tab
52 Inner Surface of Tab or Inner Surface of Base of Tab or Inner Surface of Actuator Channel
54 Base of Tab
56 Actuator Channel
60 Actuator
61 Body of Actuator
62 Pad of Actuator Body
64 Control Surface of Actuator
64a Control Surface of Actuator
64b Control Surface of Actuator
66 Locking Pawl
70 Flange
72 Cam Plate
74 Upper Cam Surface
75 Flange
76 Cam Plate
78 Upper Cam Surface
80 Leading Edge of Flange
82 Hinge
84 Inner Face of Flange
86 Outer Surface of Flange or Outer Face of Flange
E Leading Edge of Device
110 Device
120 Frame
122 Access Port
126 First Longitudinal Side of Access port
127 Second Longitudinal Side of Access port
140a Side Member of Frame
140b Side Member of Frame
144a Side Edge of Side Member
144b Side Edge of Side Member
145a Suture Pad
145b Suture Pad
152a Inner Surface of Actuator Channel
152b Inner Surface of Actuator Channel 154 Base of Tab
154a First Actuator Guide
154b Second Actuator Guide
155 Ears of Actuator Guide
156a First Actuator Channel
156b Second Actuator Channel
160 Actuator
161 Actuator Body
161a First Lateral Segment of Actuator
161b Second Lateral Segment of Actuator
162 Pad
163a Rail of Lateral Segment of Actuator
163b Rail of Lateral Segment of Actuator
166a Locking Pawl
166b Locking Pawl
168 Lower Surface of Pad
170 Flange
170' Flange
175 Flange
175' Flange
180 Leading Edge of Flange
180' Leading Edge of Flange
190a First Lateral Member
190b Second Lateral Member
192b Gear Teeth
194a Fixed End of First Lateral Member
194b Fixed End of Second Lateral Member
196a Free End of First Lateral Member
196b Free End of Second Lateral Member
198a Pivot Pin
198b Pivot Pin
200a Carriage
200b Carriage
202a Carriage Body
202b Carriage Body
204a Pivot Pin
204b Pivot Pin
210a Gear Handle
210b Gear Handle
212a Locking Pin
212b Locking Pin
E' Leading Edge of Device FIGS. 1–12 illustrate one currently preferred embodiment of the present invention. This surgical access device 10 includes a frame 20 having an access port 22, which extends therethrough. This access port 22 can take any desired shape or dimension to achieve a particular clinical objective. For example, the access port 22 can be circular, elliptical, or square. In the illustrated embodiment, though, the access port 22 is generally rectangular in shape, having a longitudinal length greater than its transverse width. Such a design is particularly useful when utilizing the access port 22 in a patient's intercostal space because the distance between the ribs will effectively limit the width of the device 10. The dimensions of this access port 22 will vary significantly depending on the body cavity being accessed and the reason for such access. If one is utilizing the access port 22 to gain access to a patient's thoracic cavity through an incision through the intercostal space, typical dimensions of the access port 22 for an adult patient would be on the order of 2.5 inches (about 6.3 cm) long and 1.5 inches (about 3.8 cm) wide.

Figure 2:
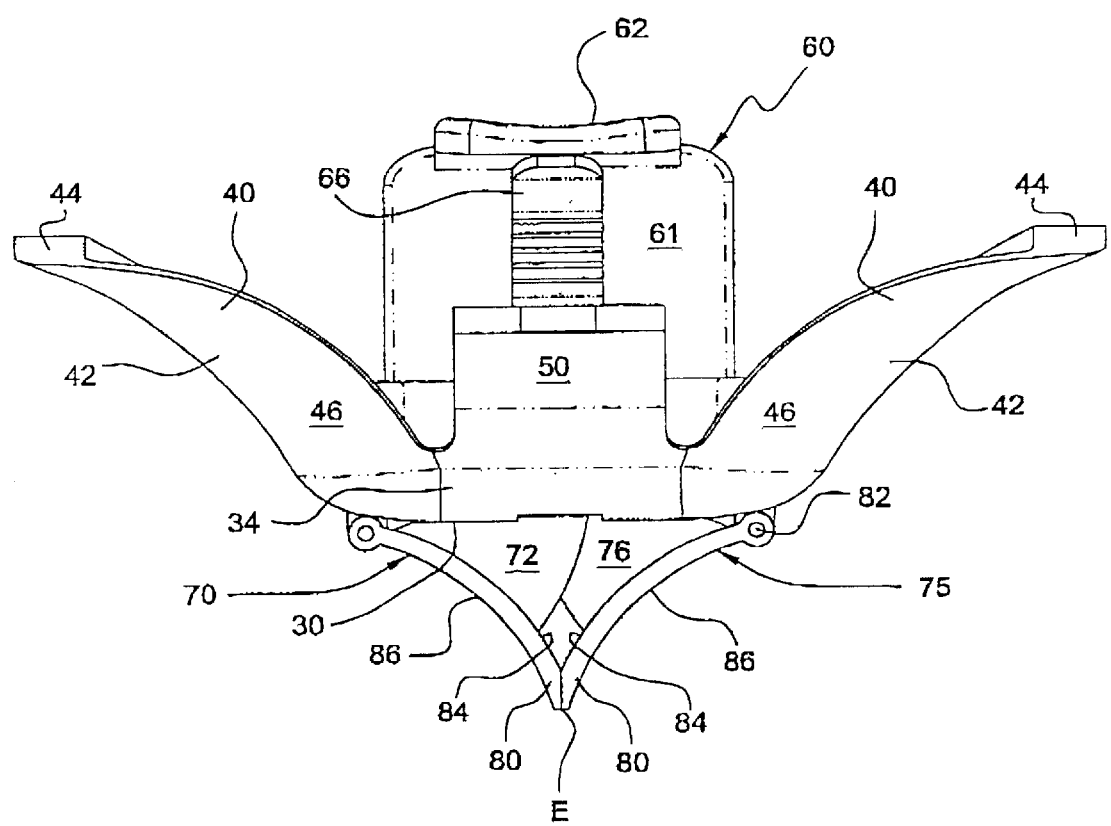
FIG. 2 is an end view of the access device of FIG. 1.
Figure 3:
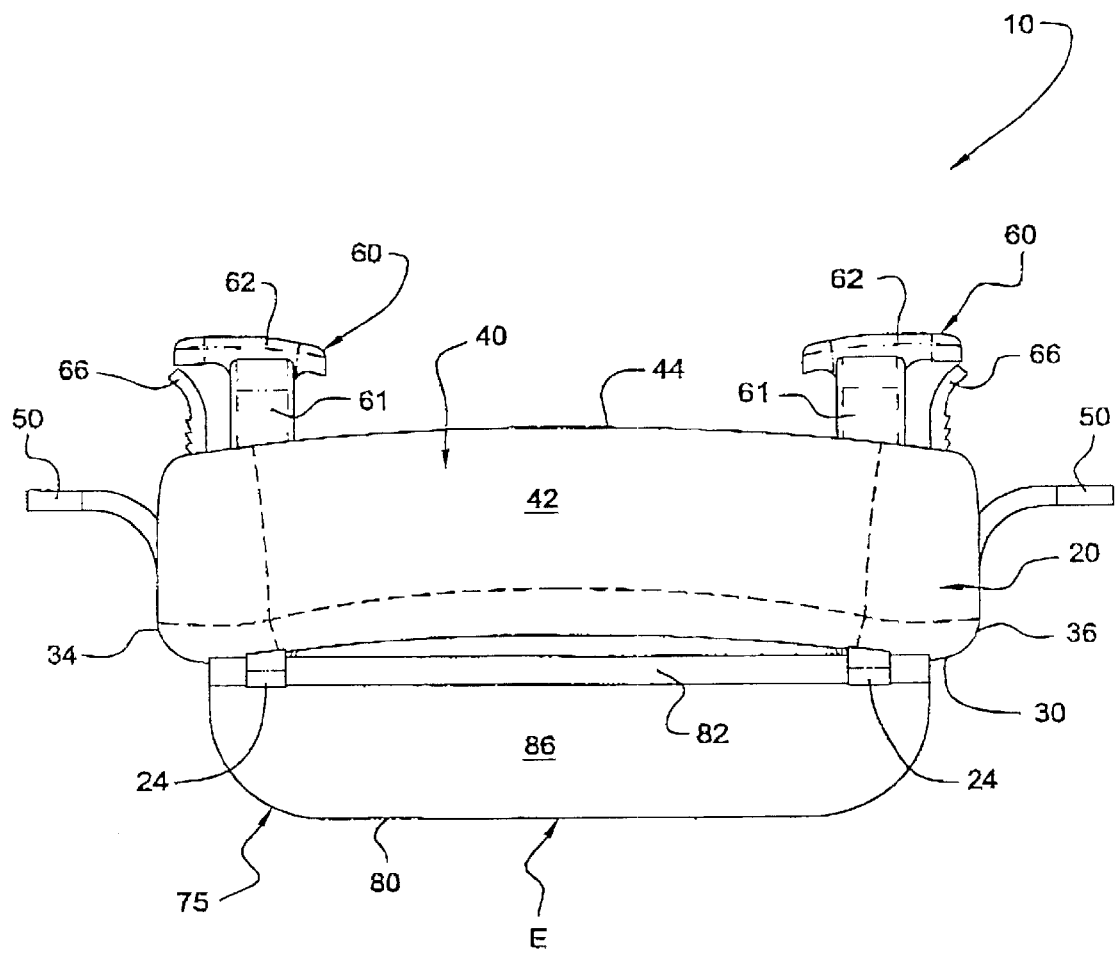
FIG. 3 is a side view of the access device of FIG. 1.
Figure 4:
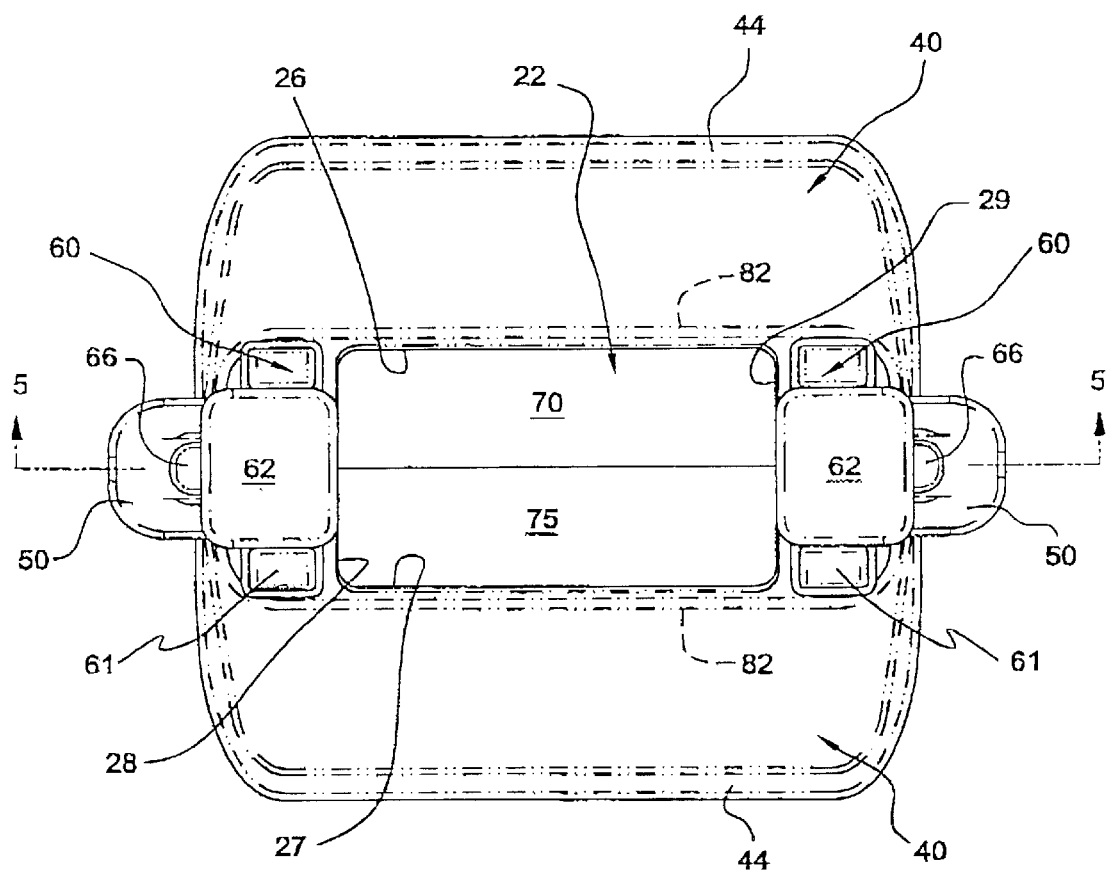
FIG. 4 is a top view of the access device of FIG. 1.
Figure 5:
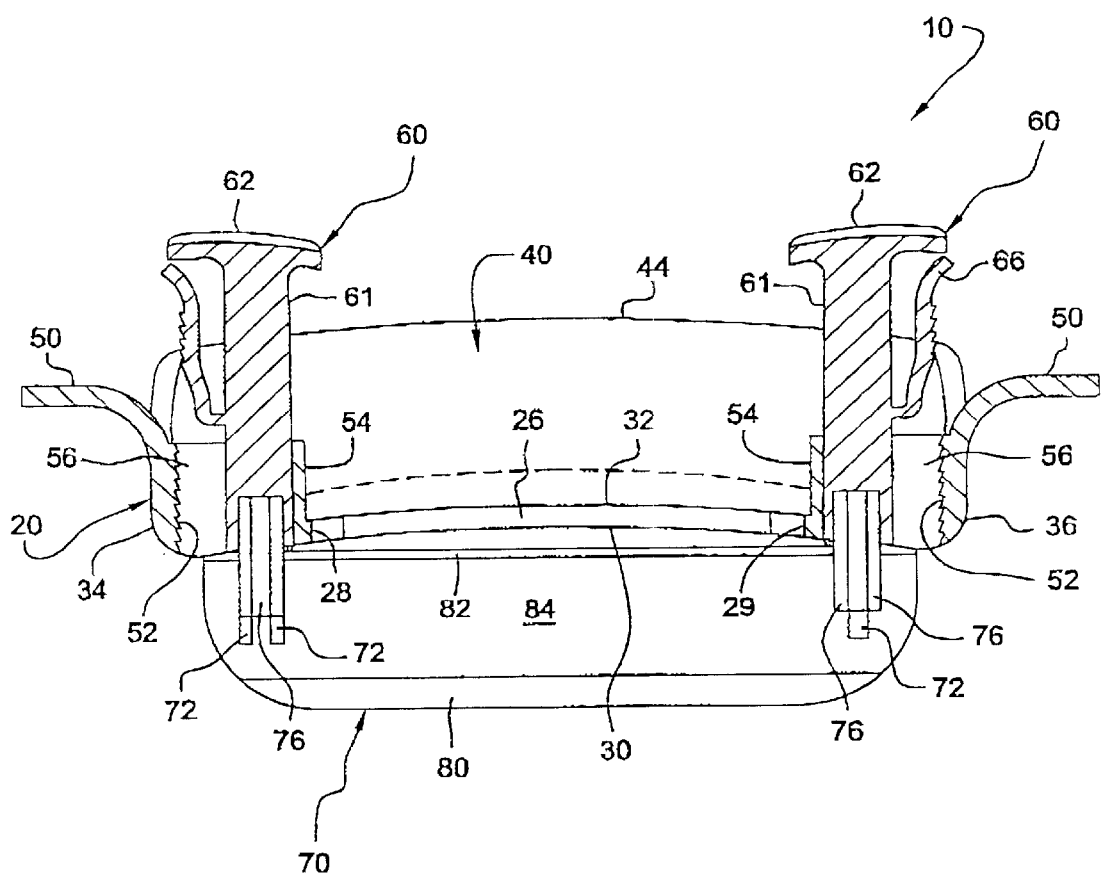
FIG. 5 is a cross sectional view taken along line 5—5 of FIG. 4.
Figure 6:
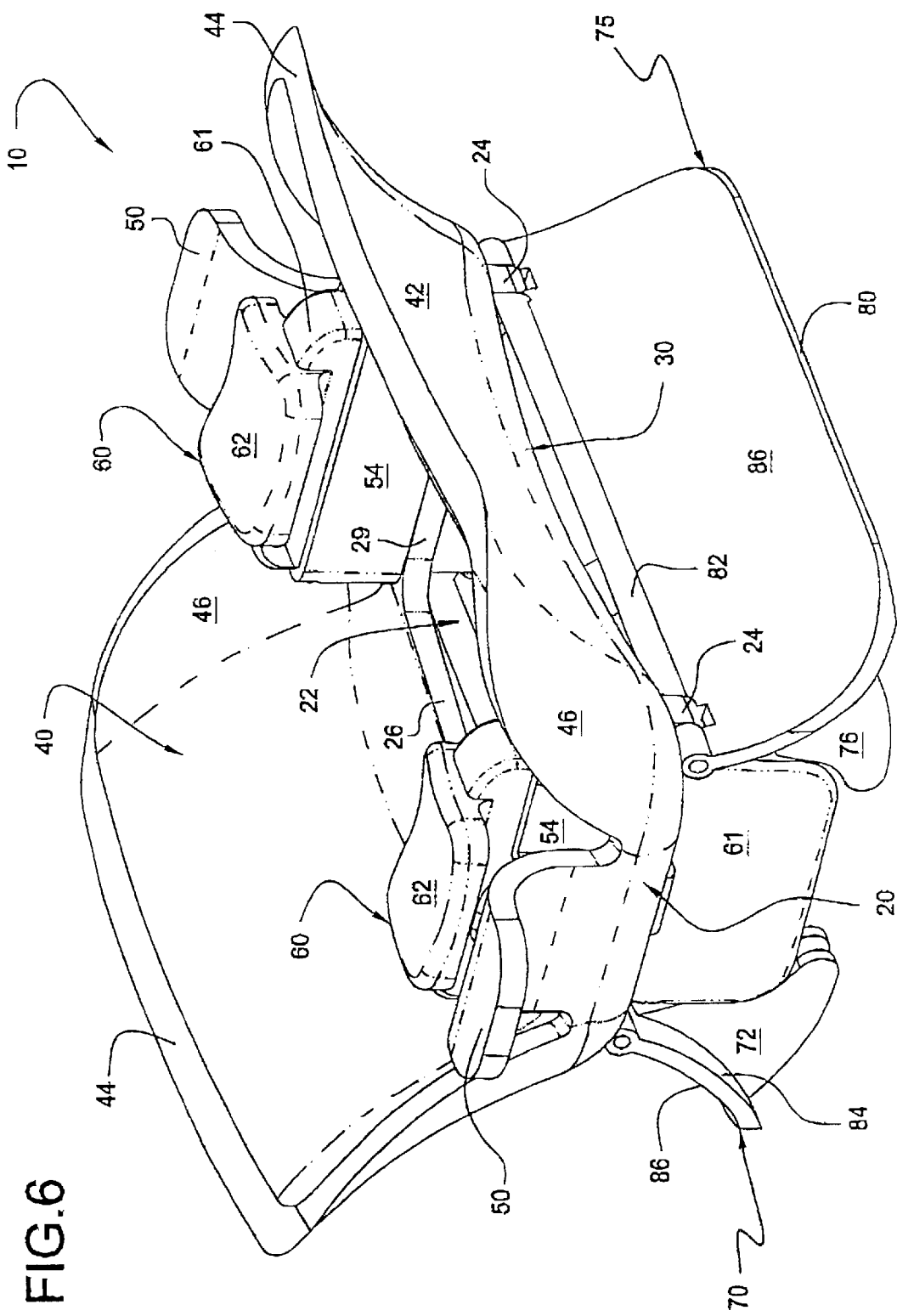
FIG. 6 is a top perspective view of the access device of FIG. 1, but wherein the flanges are in a retraction position.

The frame 20 has a lower surface 30 and an upper surface 32 (best seen in FIGS. 4 and 5). In one simplified embodiment, the frame 20 is generally rectangular in shape and is substantially planar. In the embodiment shown in FIGS. 1–12, though, the frame 20 is curved both longitudinally and laterally. As best seen in FIG. 3, the lower surface 30 of the frame 20 is curved in a longitudinal direction, defining a generally concave shape of that lower surface 30. This curvature may be optimized so that it will generally track the anticipated degree of curvature of the patient's chest when the surgical access device 10 is properly seated in the intercostal space (as described more fully below).

The frame 20 can be more radically curved in a transverse direction. As best seen in FIG. 2, the frame 20 has a pair of wings 40, with one wing 40 extending upwardly at an angle from either side of a central portion (unnumbered) of the frame 20. Desirably, the access port 22 is defined entirely within boundaries of this central portion (unnumbered). In the illustrated embodiment (as best seen in FIGS. 1 and 4), the access port 22 extends right up to the lateral margins of the central portion (unnumbered) so that each wing 40 extends at an angle upwardly from a position adjacent one of the longitudinal sides 26, 27 of the access port 22.

Each of the wings 40 includes a generally concave outer surface 42. As shown in FIG. 2, the outer surface 42 of the wing 40 curves relatively gradually upwardly from the lower surface 30 of the frame 20 to the upper edge 44 of the wing 40. As will be explained more fully below, the wings 40 are well suited to keep outer layers of the tissue in which the incision is made away from the access port 22. Desirably, this curvature is generally parabolic, with a steeper upward incline adjacent the central portion (unnumbered) of the frame 20 than adjacent the upper edge 44 of the wing 40. As a matter of fact, the outer surface 42 of the wing 40 may be very nearly vertical immediately adjacent the central portion (unnumbered) of the frame 20 while the outer surface 42 is virtually horizontal adjacent the upper edge 44. This will make it easier for the access port 22 to be seated below the upper surface of the tissue in which the incision is made without unduly restricting the physician's ability to freely manipulate tools through the access port 22.

As best seen in FIG. 1, each side (unnumbered) of the wing 40 is provided with a curved side 46. The curved side 46 tapers transversely from its lower end (unnumbered) (adjacent the central portion (unnumbered) of the frame 20) up to the upper edge 44 of the wing 40. While these sides 46 can be omitted, the sides 46 do help provide the device 10 with a relatively smooth, atraumatic surface to minimize any unnecessary trauma to the tissue at the surgical site. Care should be taken to minimize interference with the physician's access to the body cavity through the access port 22, though.

Each of the first and second ends (28 and 29, respectively) of the frame 20 includes a manually graspable tab 50. The manually graspable tab 50 desirably extends longitudinally outwardly from the end 28, 29 of the frame 20 with which it is associated. The tab 50 should extend far enough beyond the rest of the frame 20 to permit an operator to place a finger under the manually graspable tab 50 to deploy the flanges 70, 75 in a manner described below. Each of the manually graspable tabs 50 has a base 54 that has an actuator channel 56 extending downwardly therethrough. This actuator channel 56 is sized to slidably receive an actuator 60 therein. While the operation of the actuator 60 will be discussed in more detail later, it is worth noting that the manually graspable tab 50 and the actuator 60 both may include a mechanism serving as a ratchet fitting to limit upward movement of the actuator 60 within the actuator channel 56. In the embodiment illustrated in FIGS. 1–12, this ratchet fitting comprises a series of teeth provided on an inner surface 52 of the actuator channel 56 (best seen in FIGS. 5 and 10), with these teeth engaging mating teeth on a portion of the actuator 60 to hold the actuator 60 in a lower position.

As noted above, a pair of flanges 70, 75 extends downwardly from the lower surface 30 of the frame 20. More specifically, a first flange 70 is carried on the lower surface 30 of the frame 20 adjacent the first longitudinal side 26 of the access port 22 while a second flange 75 is carried on the lower surface 30 of the frame 20 adjacent the second longitudinal side 27 of the access port 22. Each of these flanges 70, 75 is pivotable between an insertion position (shown in FIGS. 1–5) and at least one retracting position (one of which is shown in FIGS. 6–10).

The pivotable connection between the flanges 70, 75 and the frame 20 can be achieved in any desirable fashion. In the illustrated embodiment, the upper edge of each flange 70, 75 defines a hinge 82. This hinge 82 is adapted to mate with one or more hinge fittings 24 carried by the lower surface 30 of the frame 20. As noted above in the illustrated embodiment, the lower surface 30 of the frame 20 is curved in a longitudinal direction. This means that the middle of the central portion (unnumbered) of the frame 20 is spaced above the horizontal level of the first and second ends 28, 29 of the access port 22. In order to ensure relatively smooth pivoting about a well-defined pivot access, the hinge 82 of each frame 20 is desirably attached to two spaced-apart hinge fittings 24, with one hinge fitting 24 being positioned adjacent either end (unnumbered) of the flange 70, 75. This will permit the hinge 82 to pivot freely without interference from the lower surface 30 of the frame 20 while maintaining mechanical simplicity. While these hinge fittings 24 can take any desirable form, they may simply comprise a downwardly extending body (unnumbered) with a pair of laterally extending hubs (not shown) which are received in mating recesses (not shown) provided on opposed faces (unnumbered) of the hinge 82. Such snap-fit hinges 82 are well known in the art and other alternative structures will be readily apparent to the average practitioner.

These two hinges 82 define pivot axes for their respective frames 20. The hinges 82 are generally parallel to one another and they are both carried on the lower surface 30 of the frame 20. As a result, the two pivot axes together define a plane, which is generally horizontal in the position shown in FIGS. 1–12. As explained below, the leading edge E of the surgical access device 10 is inserted into an incision in the patient's skin in a direction, which is generally vertical in these same drawings. As a consequence, the plane defined by these two horizontal axes is generally perpendicular to the direction in which the leading edge E of the device 10 is inserted into that incision.

Each of the first and second flanges 70, 75 has a leading edge 80 which extends longitudinally along the portion of the flange 70, 75 spaced farthest from the hinge 82. When the two flanges 70, 75 are in their insertion position, the leading edges 80 thereof will be positioned immediately adjacent one another. Optimally, the leading edges 80 directly abut one another.

The embodiment of FIGS. 1–12 utilizes a bevel adjacent the leading edge 80 of each flange 70, 75 to permit the leading edges 80 to be positioned flush with one another. As best seen in FIG. 2, when these beveled faces (unnumbered) of the flanges 70, 75 abut one another, they define a relatively narrow elongate leading edge E of the surgical access device 10. Desirably, the leading edges 80 of the two flanges 70, 75 and the leading edge E of the device 10 are generally parallel to the hinges 82 of the flanges 70, 75 and the respective pivot axes the hinges 82 define.

Each of these flanges 70, 75 may be generally flat, planar structures. The preferred embodiment shown in FIGS. 1–12 employs curved flanges 70, 75, however. In particular, each flange 70, 75 may have a convex inner face 84 which is oriented toward the access port 22 when the flange 70, 75 is in its insertion position (FIGS. 1–5). More importantly, though, the outer face 86 of each flange 70, 75 is generally concave. This concave outer face 86 is adapted to contact tissue into which the device 10 is inserted and to retain the tissue between the flange 70 or 75 and the lower surface 30 of the frame 20. More particularly, when the flanges 70, 75 are in a retracting position (one of which is shown in FIGS. 6–10), a patient's tissue will be disposed in the space between the concave outer face 86 of each flange 70, 75 and the outer surface 42 of the adjacent wing 40. This will both help anchor the surgical access device 10 in place and, as explained more fully below, pull the frame 20 downwardly to better seat the device 10 within the incision.

Some prior art retraction devices utilize curved blades. For example, U.S. Pat. No. 4,765,311 (Kulik et al.) and U.S. Pat. No. 5,125,396 (Ray), both of which are mentioned above in the background discussion, each provide a retractor with blades extending downwardly into an opening. These blades are defined as curved surfaces, which are essentially arcs of an elongate tube. In the Kulik et al. and Ray devices, though, the curved blades are curved about a vertical axis, i.e., an axis which is generally perpendicular to a line tangent to the tissue in which it is being inserted and generally parallel to the direction in which the device is inserted into the incision in the patient's tissue.

The flanges 70, 75 of the present invention, however, are curved in a different orientation. The shape of each of the flanges 70, 75 may be described as a series of longitudinally extending lines, each of which is parallel to and spaced from a common axis. This common axis extends horizontally, i.e., it is generally parallel to the pivot axis of the respective flange 70, 75.

Figure 7:
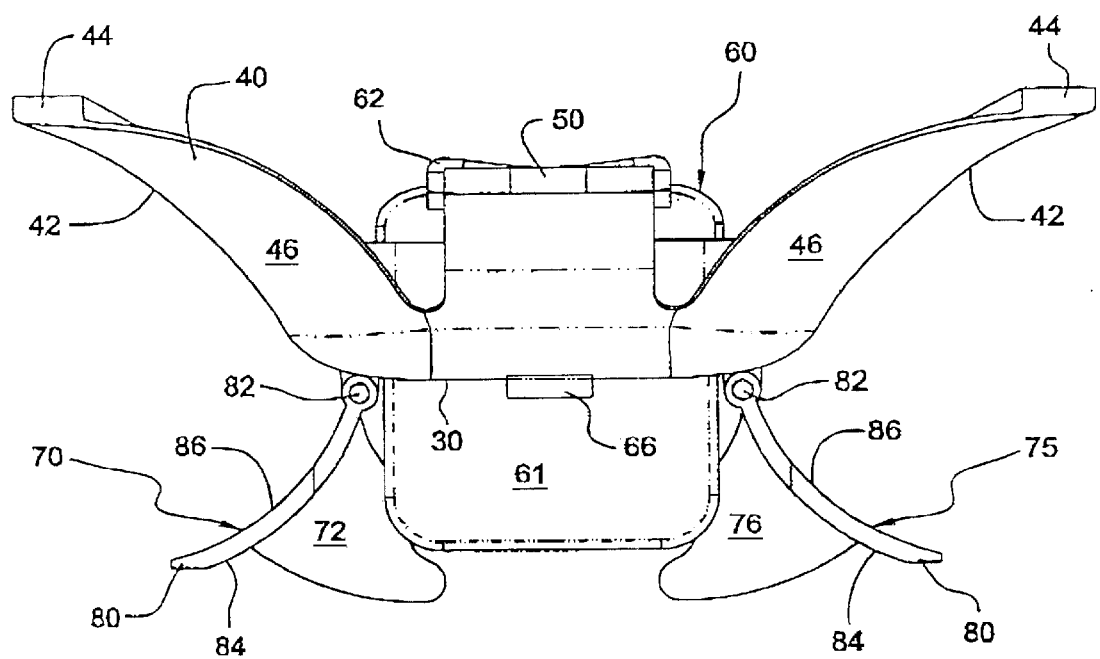
FIG. 7 is an end view of the access device of FIG. 6.
Figure 8:
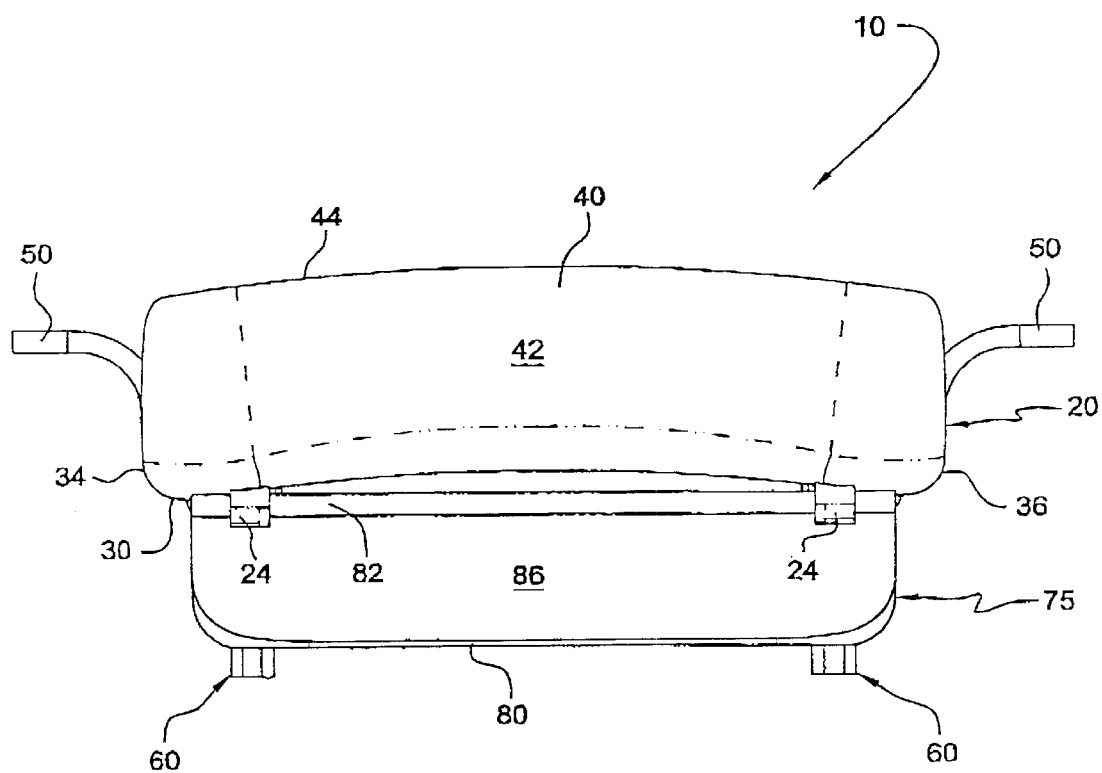
FIG. 8 is a side view of the access device of FIG. 6.
Figure 9:
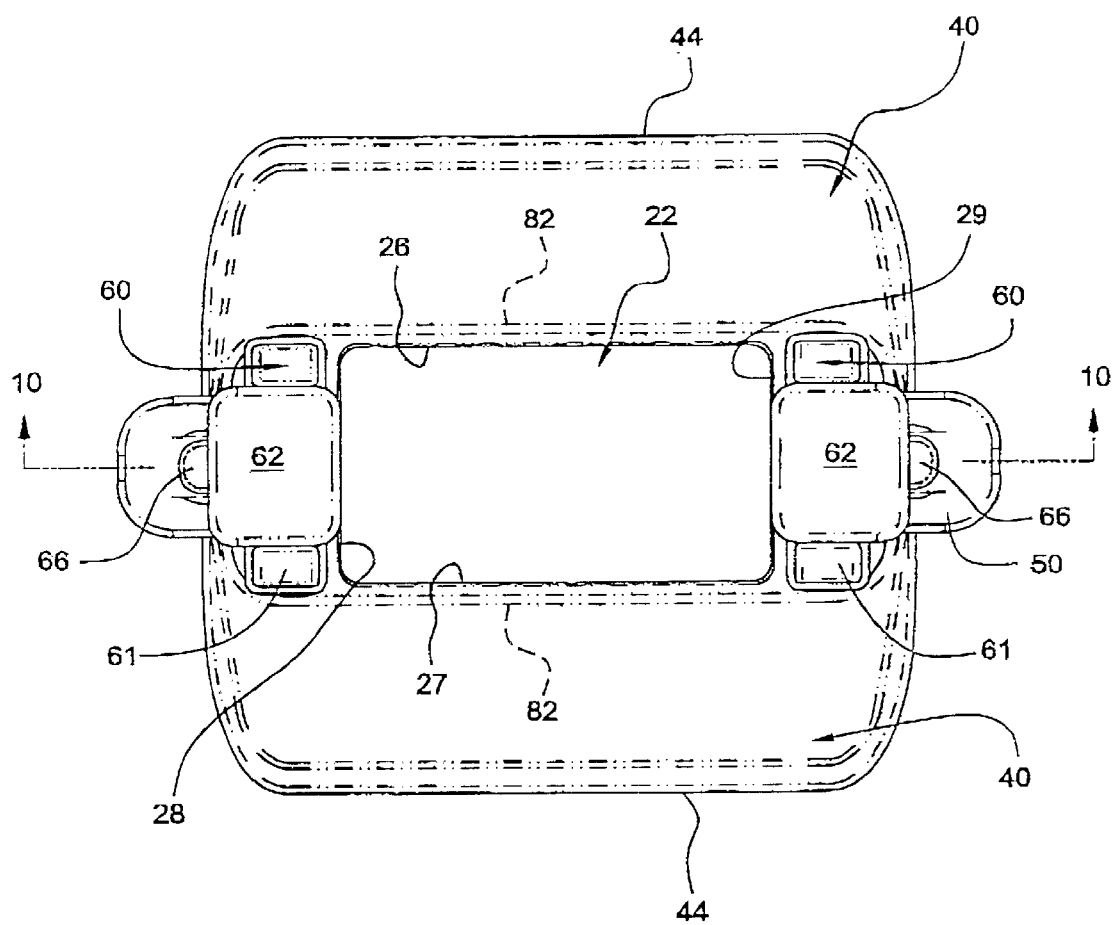
FIG. 9 is a top view of the access device of FIG. 6.

The orientation of the concave outer face 86 of the flanges 70, 75 with respect to the frame 20 will change as the flanges 70, 75 move from their insertion position to their various retracting positions. As best seen in FIG. 2, when the flanges 70, 75 are in their insertion position, the outer face 86 is concave in a direction, which faces outwardly and downwardly away from the lower surface 30 of the frame 20. When the flanges 70, 75 are pivoted well away from their insertion position into one of their more distant retracting positions (e.g., as shown in FIG. 7), though, the outer face 86 of the flanges 70, 75 are concave in a direction oriented generally upwardly. This orientation will facilitate grasping the bottom of the tissue in which the device 10 is inserted and urging the tissue upwardly toward the adjacent wing 40 of the frame 20.

The flanges 70, 75 can be moved from their insertion position to their various retraction positions by any desired means. In its simplest form, the surgical access device 10 could simply comprise the frame 20 and the flanges 70, 75, allowing the operator to manually move the flanges 70, 75 apart, e.g., by pressing a finger against the inner faces 84 of the flanges 70, 75. This will not give the operator very much leverage, though, and the force the operator can practically exert on the flanges 70, 75 with a finger may well be insufficient to retract the tissue with the flanges 70, 75 to seat the device 10.

In addition, if the flanges 70, 75 move the tissue outwardly to increase the size of the opening through the tissue, the tissue will tend to urge the flanges 70, 75 back toward their insertion position. The operator could either continue to hold the flanges 70, 75 in their retraction position or wedge something between them to maintain that position, but that is rather impractical. The surgical access device 10 desirably includes some mechanism for retaining the flanges 70, 75 in at least one retraction position to free the operator's hands and maximize the opening provided by the access port 22. For example, the hinges 82 may be designed to lock the flanges 70, 75 in at least one retraction position once the flanges 70, 75 are spread far enough apart. In order to permit the physician to remove the device 10 without destroying it, some mechanism for releasing the hinges 82 should also be provided.

FIGS. 1–12 illustrate one particularly preferred embodiment, which utilizes a separate actuator 60. As noted above, this actuator 60 is designed to be slidably received in an actuator channel 56 provided in the base 54 of the manually graspable tabs 50. The illustrated actuator 60 includes a body 61 with a manually engagable pad 62 provided at the top of the body 61. The body 61 should be designed to fairly snuggly fit in the actuator channel 56 to ensure that it travels primarily upwardly and downwardly within the channel 56 without too much lateral motion.

The embodiment of FIGS. 1–12 employs a body 61 which has a smooth outer surface (unnumbered) received in a relatively smooth actuator channel 56. FIGS. 13–27, discussed in more detail below, show an alternative embodiment of the invention. In this embodiment, the actuator channel 156a has a pair of parallel recessed tracks. The body 161 of the actuator 160 has a pair of parallel, spaced-apart rails 163a and 163b which are adapted to be slidably received within the recessed tracks of the base 154. As an operator pushes downwardly against the pad 162 at the top of the body 161, the rails 163a and 163b and recessed tracks will help guide the actuator 160 downwardly along a vertical path. While the actuator 160 in FIGS. 13–27 is split into separate lateral portions, it should be understood that the same concept of rails 163a, 163b guided in tracks can be used to better guide a single, integral actuator 60 such as that illustrated in FIGS. 1–12.

The actuator 60 can be adapted to directly engage the inner face 84 of each of the flanges 70, 75 to urge them out of the way. If so desired, though, a more complex cam arrangement can be utilized to enhance mechanical advantage of the actuator 60 and improve the ability of the operator to retract tissue with the flanges 70 and 75.

In the illustrated embodiment, each flange 70, 75 is provided with at least two cam plates 72, 76, which extend inwardly from the inner face 84 of the flange 70, 75. In particular, the first flange 70 has three inwardly extending cam plates 72 and the second flange 75 has three inwardly extending cam plates 76. As best seen in FIG. 5, at each end, the cam plate 72, 76 from one of the two flanges 70, 75 can be received between two adjacent cam plates 72, 76 from the other flange 70, 75. For example, FIG. 5 shows the flange 70 having a pair of spaced-apart cam plates 72 at the left end of the flange 70 with a single cam plate 72 at the right side of the flange 70. The second flange 75 (not itself visible in FIG. 5) has a single cam plate 76 on its left side and this cam plate 76 is received between the two adjacent cam plates 72 of the first flange 70. Conversely, the right side of the second flange 75 is provided with a pair of cam plates 76 and the single cam plate 72 of the other flange 70 is received between those two cam plates 76. This helps guide the flanges 70, 75 along a predefined path and limit tortional stress on the hinges 82. To simplify manufacturing, though, one could provide just two cam plates 72, 76 on each flange 70, 75, with one of these plates 72, 76 being positioned beneath each of the actuators 60.

Figure 11:
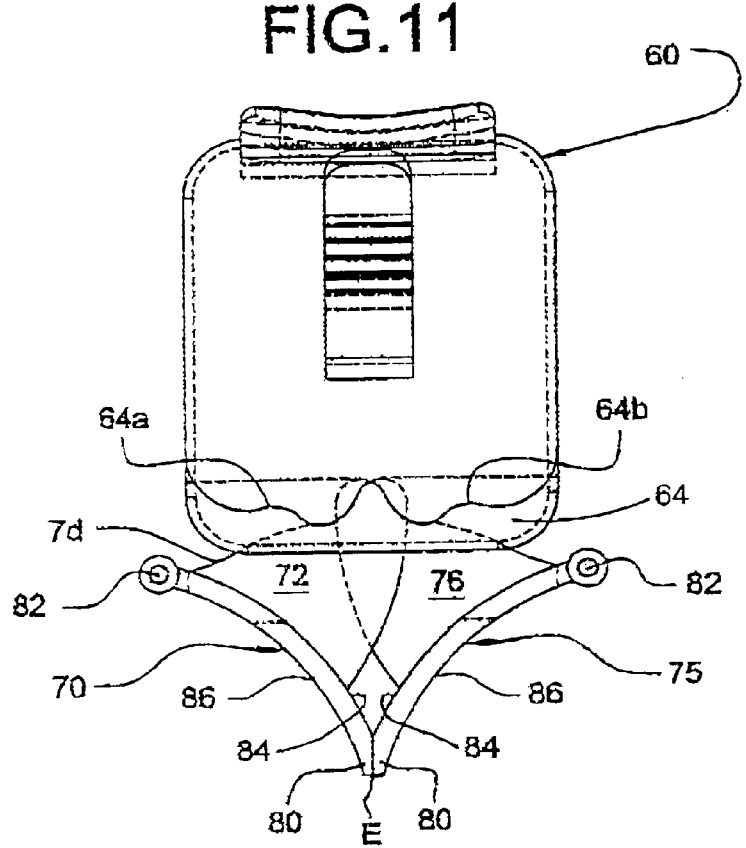
FIG. 11 is an isolational end view of a portion of the access device of FIG. 1, schemaically illustrating the engagement between an actuator and the flanges when the flanges are in their insertion position.
Figure 12:
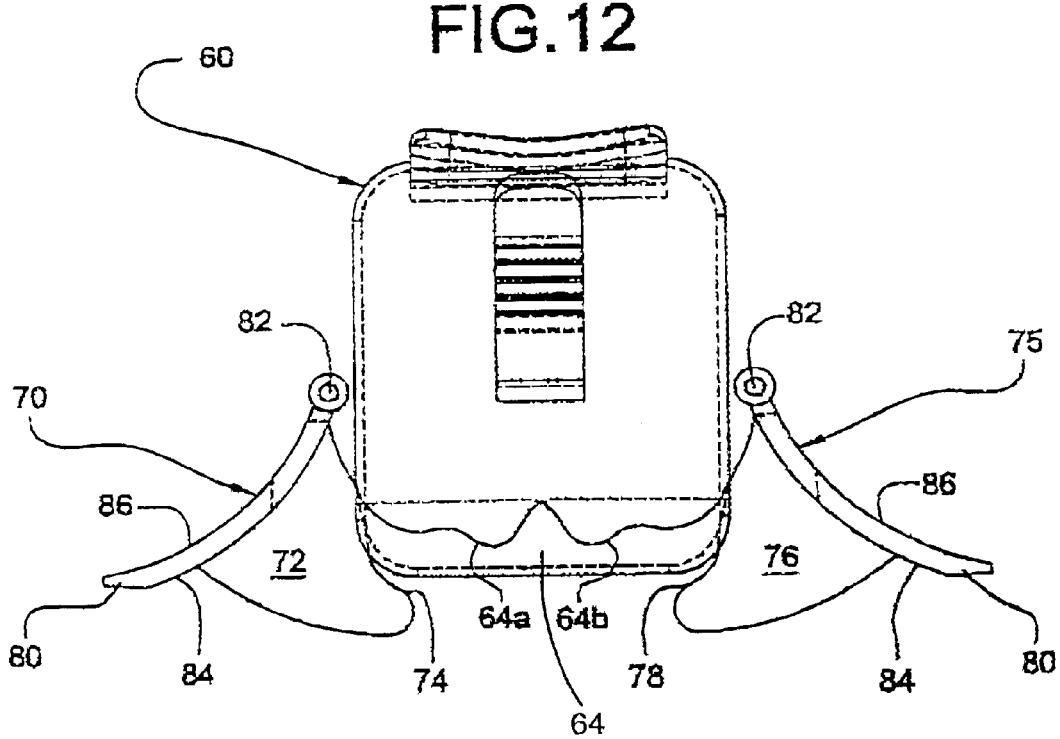
FIG. 12 isolational end view similar to FIG. 11, but schematically illustrating the engagement between the actuator and the flanges when the flanges are in a retraction position.
Figure 13:
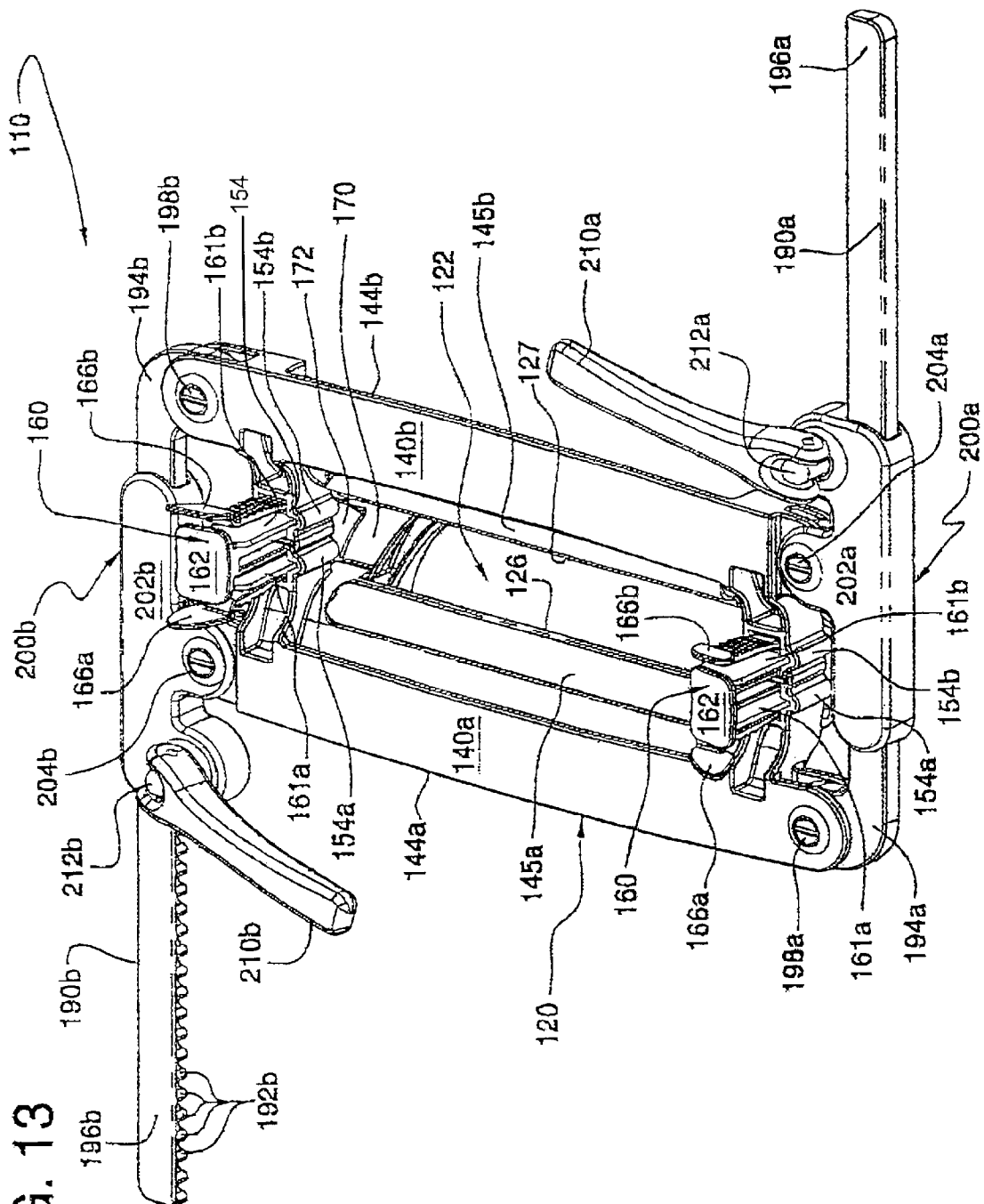
FIG. 13 is a top perspective view of a surgical access device in accordance with an alternative embodiment of the invention with the frame thereof in an insertion configuration.
Figure 14:
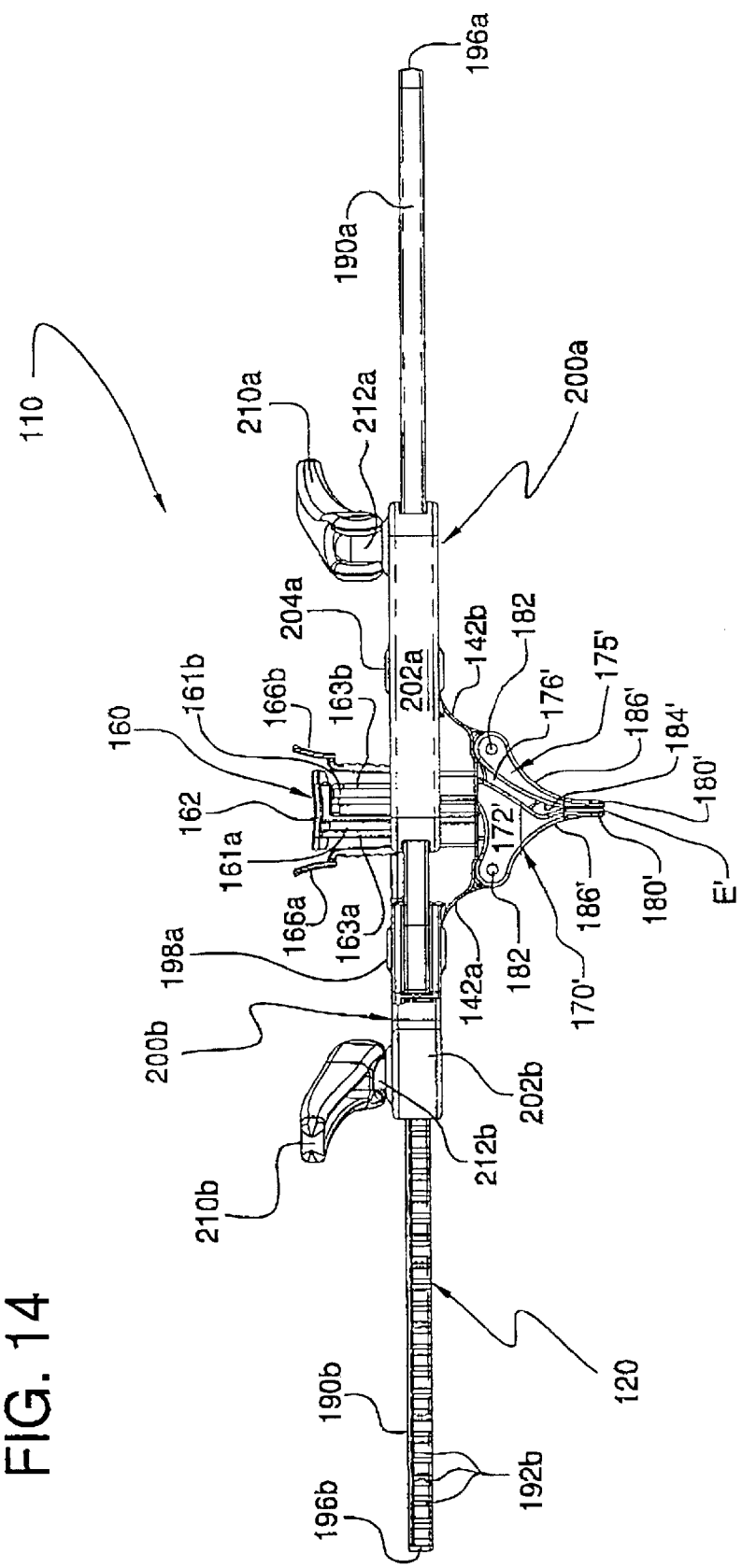
FIG. 14 is an end view of the access device of FIG. 13.

FIGS. 11 and 12 are schematic drawings showing only the actuator 60 and the flanges 70, 75 in a simplified end view. FIG. 11 shows these elements with the flanges 70, 75 in their insertion position while FIG. 12 shows the physical relationship of these elements with the flanges 70, 75 in a retraction position.

The cam plates 72 of the first flange 70 have an upper cam surface 74 while the cam plates 76 of the other flange 75 have an upper cam surface 78 which is desirably the mirror image of the cam surface 74 on the other flange 70. The lower portion of the actuator 60 is provided with a control surface 64. In the illustrated embodiment, the control surface 64 is actually divided into two effective surfaces 64a and 64b. The control surface 64a is adapted to engage the upper surface 74 of the cam plate 72 while the other control surface 64b is adapted to engage the upper surface 78 of the cam plate 76. As noted above in connection with FIGS. 5 and 10, the cam plates 72 and 76 are positioned adjacent to one another. As a consequence, these control surfaces 64a and 64b would be positioned beside one another, but can overlap one another laterally if deemed necessary.

The specific shapes of the control surfaces 64 of the actuator 60 and the upper surfaces 74, 78 of the cam plates 72, 76 can be varied as desired. The illustrated design is useful for maximizing the initial mechanical advantage when the operator first pushes downwardly on the actuators 60 to help spread the tissue apart. Once the flanges 70, 75 have been moved away from their insertion position (FIG. 11), the surfaces 74, 78 of the cam plates 72, 76 and the actuator 60 are shaped to maximize the motion of the flanges 70, 75 for the limited vertical travel of the actuator 60. A wide variety of different cam surfaces 74, 78 can be employed to achieve the specific design objectives of a given application, however.

Figure 10:
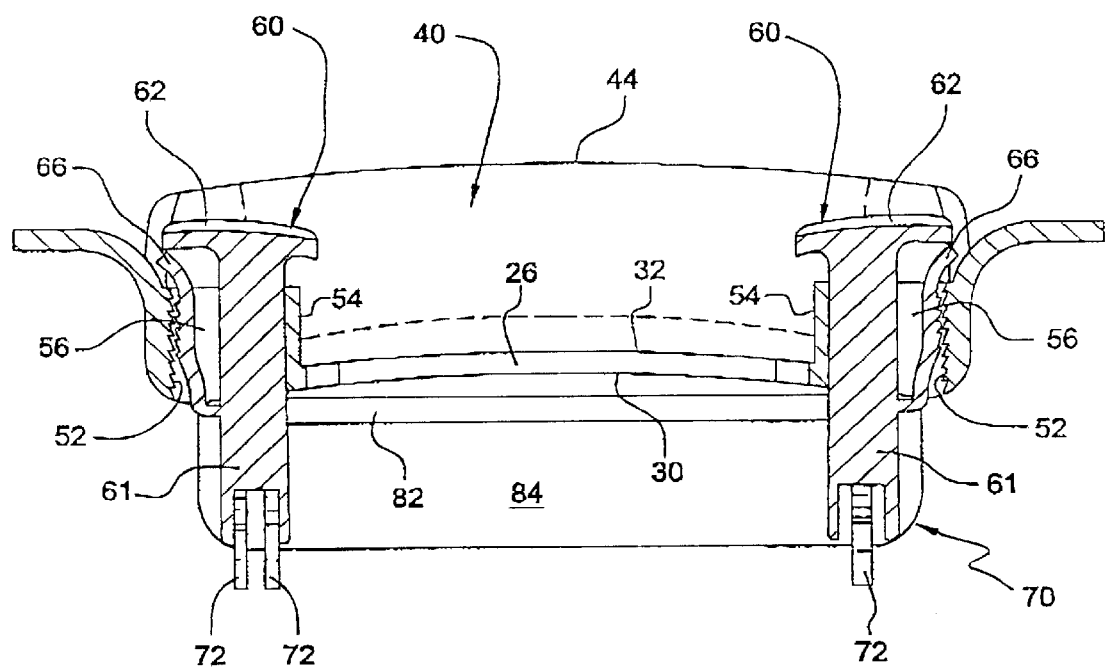
FIG. 10 is a cross sectional view taken along line 10—10 of FIG. 9.

The actuator 60 also includes a locking pawl 66 carried on its outer surface (unnumbered). This locking pawl 66 is designed to engage with a mating ratchet fitting carried by the base 54 of the manually graspable tab 50. As best seen in FIGS. 5 and 10, the locking pawl 66 is provided with teeth on its outer face and these teeth are positioned to engage the teeth on the inner surface 52 of the base 54 of the tab 50. This effectively provides mating ratchet fittings on the actuator 60 and the manually graspable tabs 50 to limit movement of the flanges 70, 75 back toward their insertion positions when the operator releases the actuator 60. In the absence of some arrangement to limit upward movement of the actuator 60, the tissue retracted by the flanges 70, 75 would tend to urge the flanges 70, 75 back toward one another, closing the opening in the tissue defined by the flanges 70, 75.

The locking pawl 66 is desirably resiliently attached to the body 61 of the actuator 60. At some point, it may be necessary to remove the surgical access device 10 from the patient's body. To do so, one can urge the locking pawls 66 inwardly away from the inner surface 52 of the associated tab 50. Doing so will disengage the teeth of the pawl 66 from the teeth of the tab 50, permitting the actuator 60 to be withdrawn upwardly.

As noted above, FIGS. 13–27 illustrate an alternative embodiment of the invention. While these two embodiments are distinct from one another, they do share some functionality. For purposes of convenience, the elements in FIGS.

13–27 which perform functions similar to elements in FIGS. 1–12 bear like reference numbers, but incremented by 100. Hence, the surgical access device 10 of FIGS. 1–12 includes a frame 20, a pair of actuators 60 and flanges 70 and 75; the surgical access device 110 of FIGS. 13–27 includes a frame 120, a pair of actuators 160 and flanges 170 and 175.

One of the primary differences between the access device 110 of FIGS. 13–27 as compared to the embodiment discussed above is that the frame 120 of the present embodiment can be manipulated to significantly alter the size and shape of the opening in the patient's tissue. In the surgical access device 10 shown in FIGS. 1–12, the frame 20 has a fixed, unalterable shape. The flanges 70, 75 depending therefrom can be moved to a variety of retracting positions to move the tissue away from the access port 22. However, the size of the access port 22 remains unchanged due to the integral structure of the upper portion (unnumbered) of the frame 20. In FIGS. 13–27, though, the size of the access port 122 can be varied as needed during the course of a procedure. This is due, in large part, to the fact that the frame 120 includes two opposed side members, 140a and 140b, and a pair of opposed lateral members, 190a and 190b. As discussed more fully below, the two sides members 140a and 140b can be moved away from one another to expand the access port 122 and grant the physician greater access to the body cavity of interest.

As with the previous embodiment, at least one flange 170 is attached to a first side member 140a of the frame 120 while a second, opposed flange 175 is attached to the other side member 140b. If so desired, these flanges 170 and 175 may be relatively long and extend along most of the length of the respective side members 140a and 140b between the two actuators 160, not unlike the flanges 70 and 75 of FIGS. 1–12.

In the embodiment shown in FIGS. 13–27, though, the surgical access device 110 employs two opposed pairs of flanges 170, 170', 175, 175'. In particular, the first side member 140a includes a pair of spaced-apart flanges 170 and 170' (see, e.g., FIGS. 15 and 18). Similarly, the second side member 140b includes a pair of spaced-apart flanges 175, 175'. While these flanges 170, 170', 175, 175' may be staggered along the length of the frame 120 it is preferred that they define two opposed pairs, with one pair comprising flanges 170 and 175 and the other pair comprising flanges 170' and 175'.

As with the prior embodiment, each of these pairs of flanges 170, 170', 175, 175' have abutting leading edges 180, 180', which define a leading edge E, E' of the surgical, access device 110. As better seen in FIGS. 14 and 17, for example, the flange 170' has a leading edge 180' and the opposite flange 175' also has a leading edge 180'. When both of the flanges 170', 175' are in their insertion position, as shown in these drawings, these leading edges 180' are positioned immediately adjacent to one another and the two flanges 170', 175' together define a leading edge E'. Similarly, the leading edge 180 of the flange 170 is positioned immediately adjacent the leading edge 180 of the opposite flange 175 to together define an upper leading edge E of the device 110 (see, e.g., FIG. 16). Optimally, when all four flanges 170, 170', 175, 175' are in their respective insertion positions, the leading edge E defined by flanges 170 and 175 is generally aligned with the leading edge E' defined by flanges 170' and 175'. In combination, these aligned edges E and E' will define an effective leading edge (unnumbered) of the surgical device 110 as a whole.

Any number of flanges 170, 170', 175, 175' can be carried by each side. While the illustrated embodiment uses two relatively short flanges 170, 170', 175, 175' carried by each side member 140a and 140b, this need not be the case. Each of the flanges 170, 170', 175, 175' could be significantly longer, leaving less space between flanges 170 and 170', for example. Alternatively, three pairs of opposed flanges could be used, with the third opposed pair being positioned between the two pairs shown in the drawings.

Figure 22:
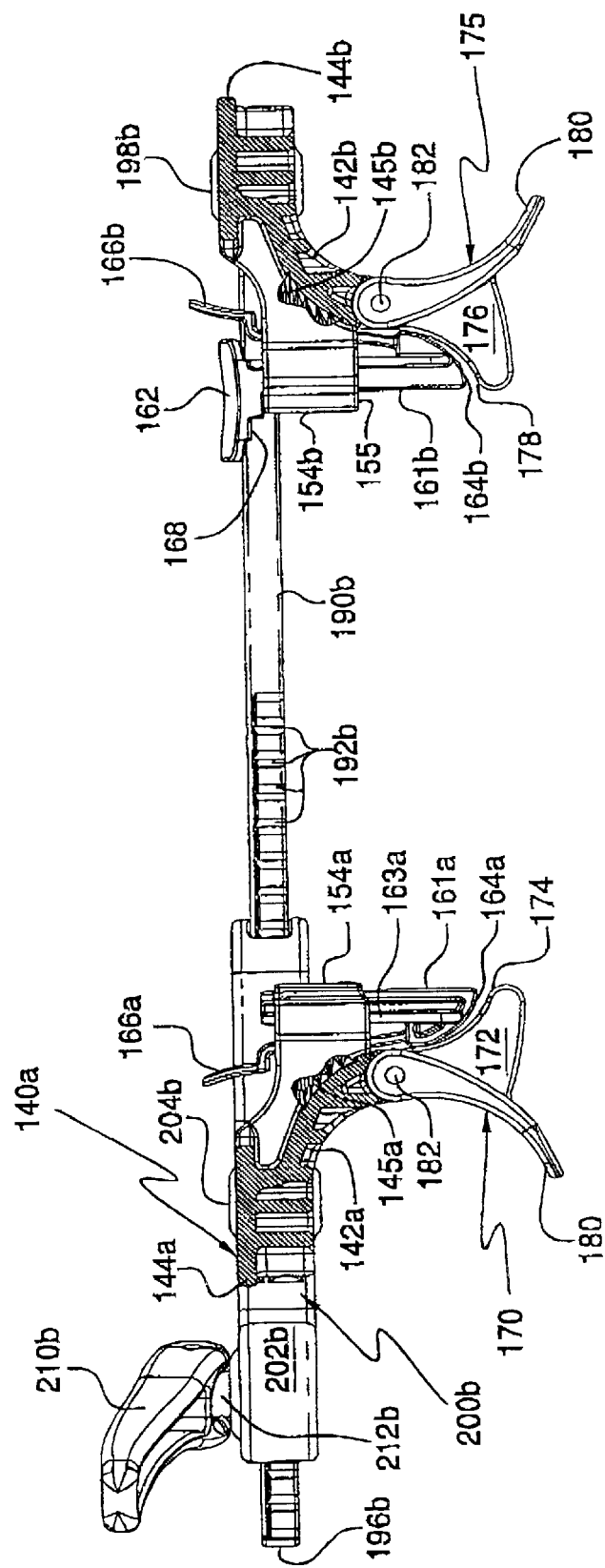
FIG. 22 is a cross sectional view taken along line 22—22 of FIG. 20.
Figure 23:
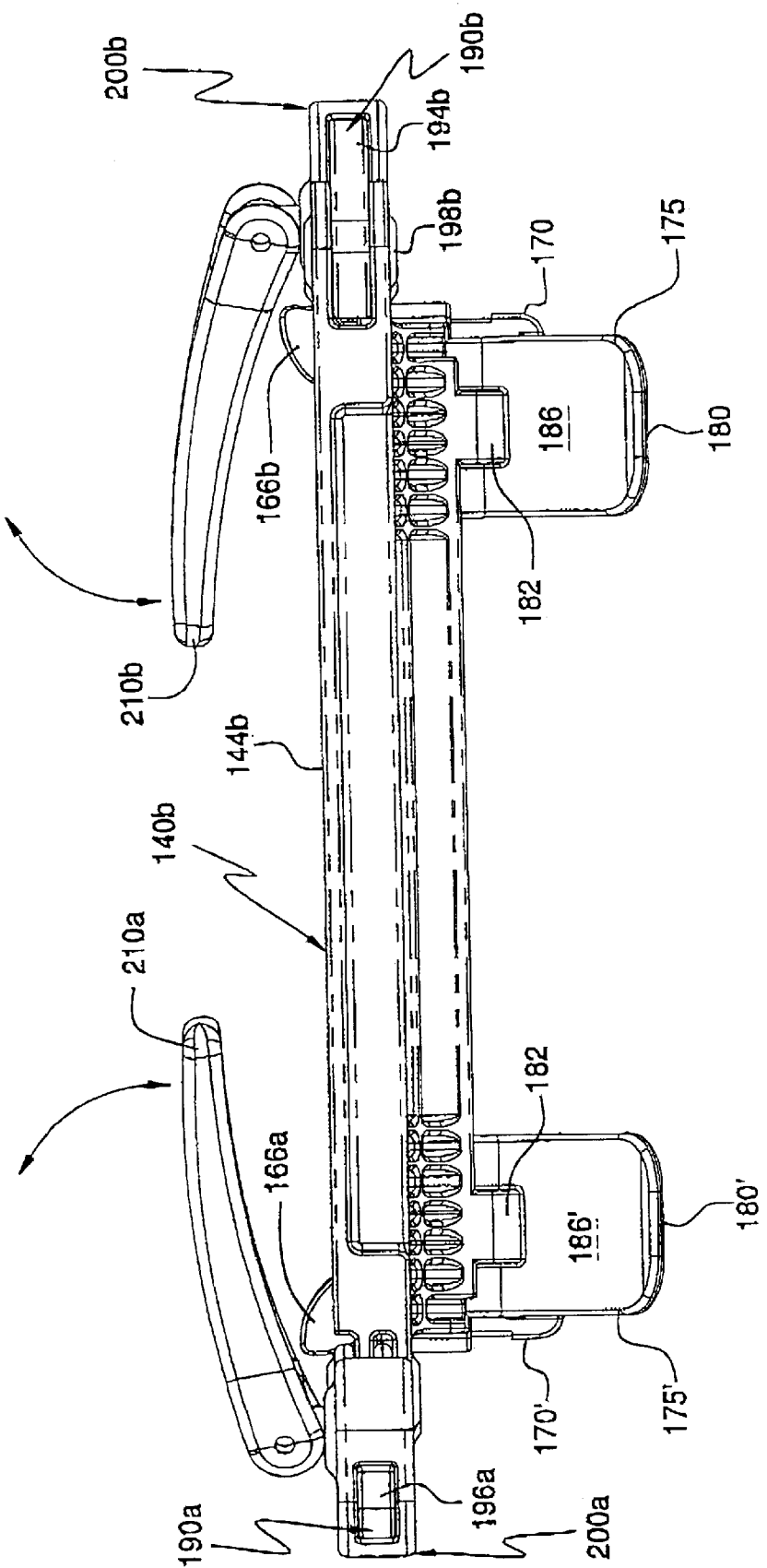
FIG. 23 is a side view of the access device of FIG. 19.
Figure 24:
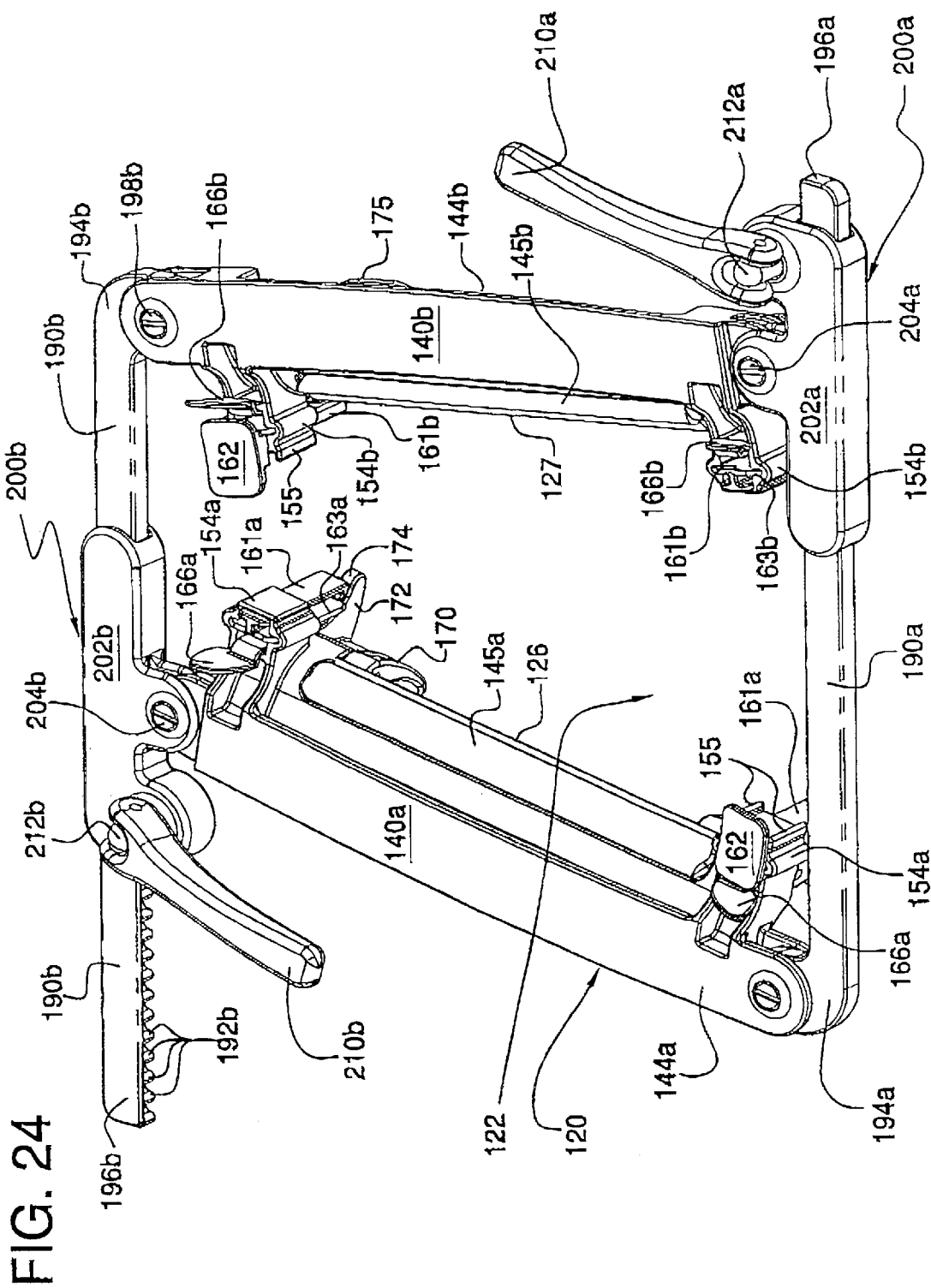
FIG. 24 is a top perspective view of the access device of FIGS. 13 and 19, but in a different retracting configuration.
Figure 25:
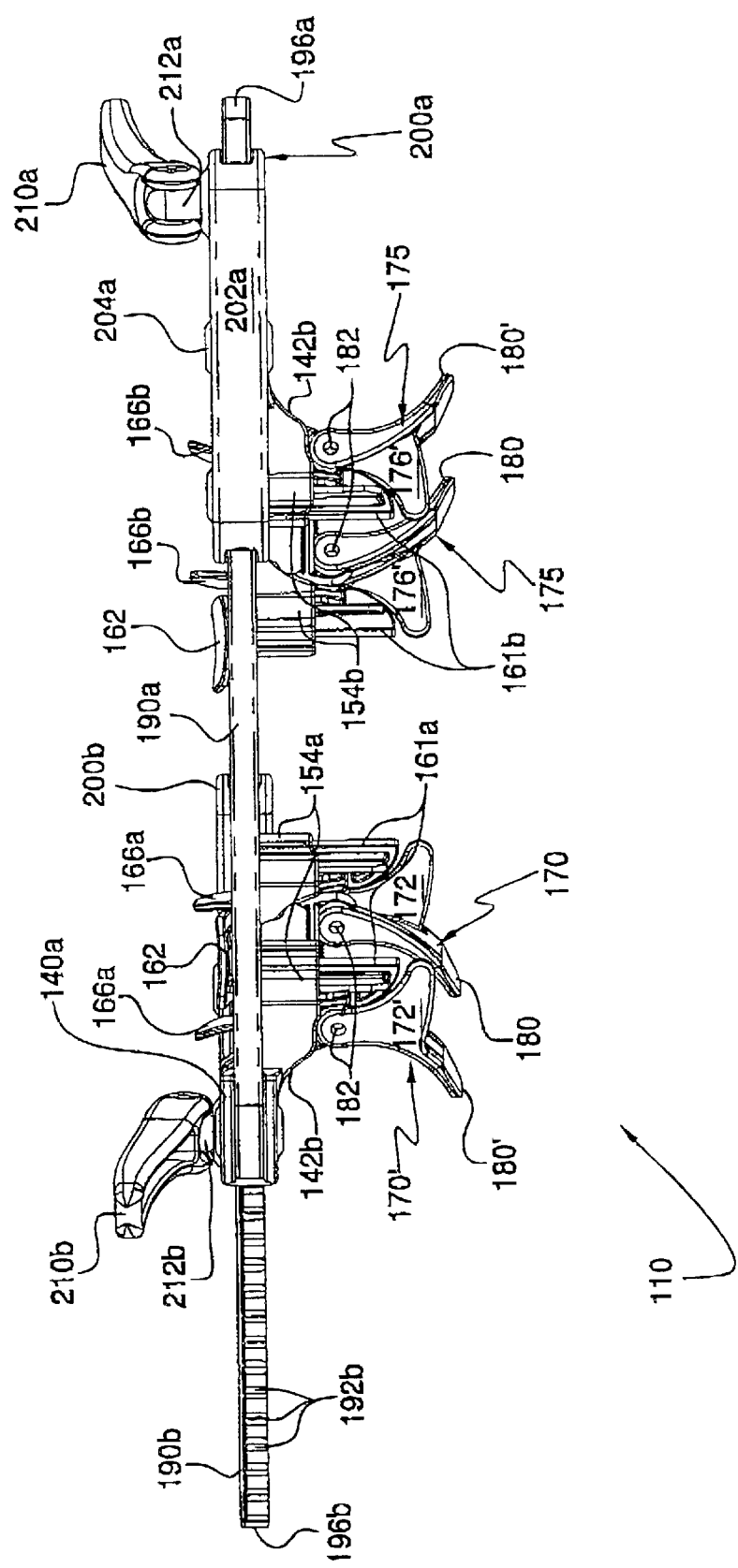
FIG. 25 is an end view of the access device of FIG. 24.
Figure 26:
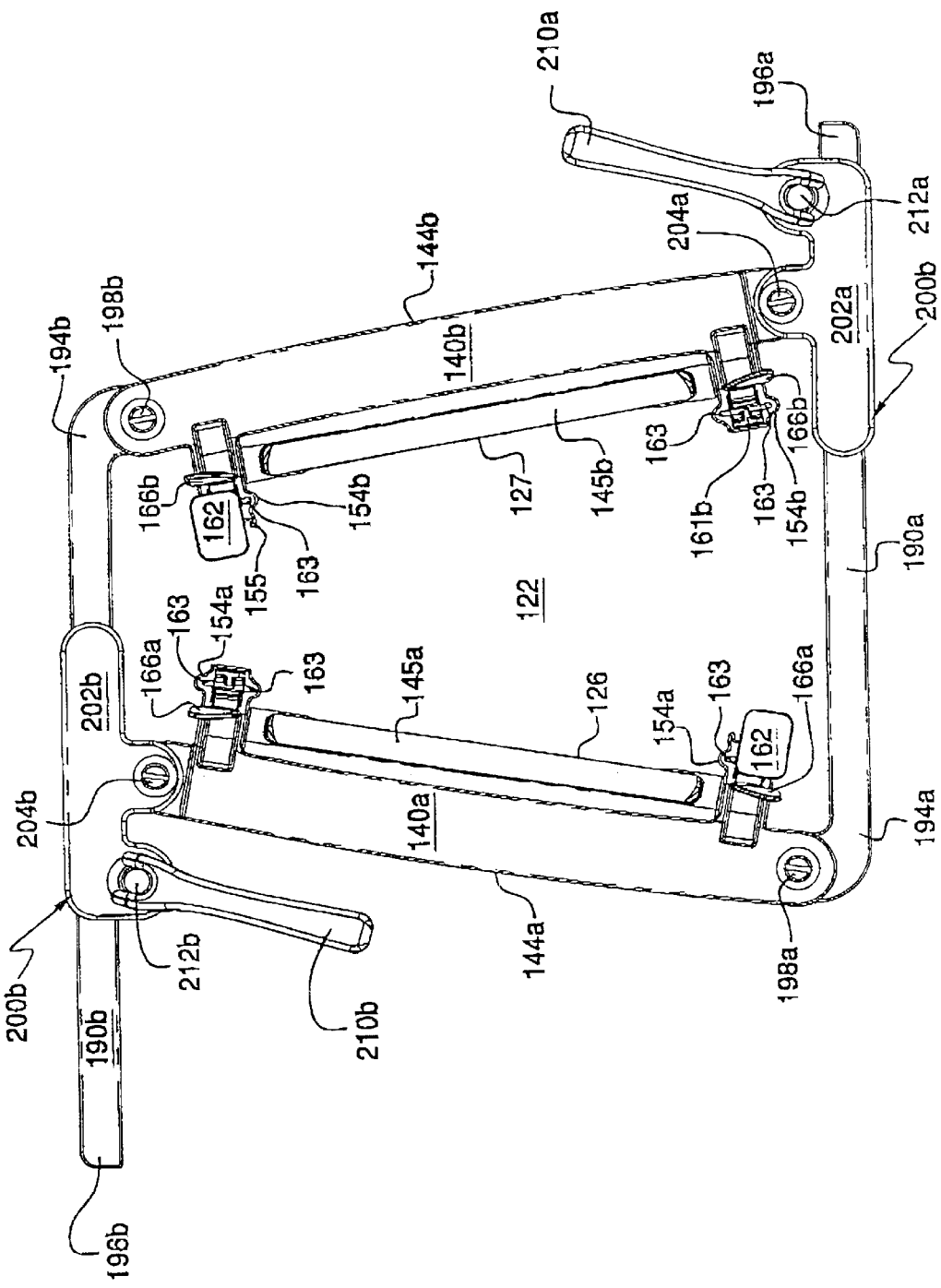
FIG. 26 is a top view of the access device of FIG. 24.
Figure 27:
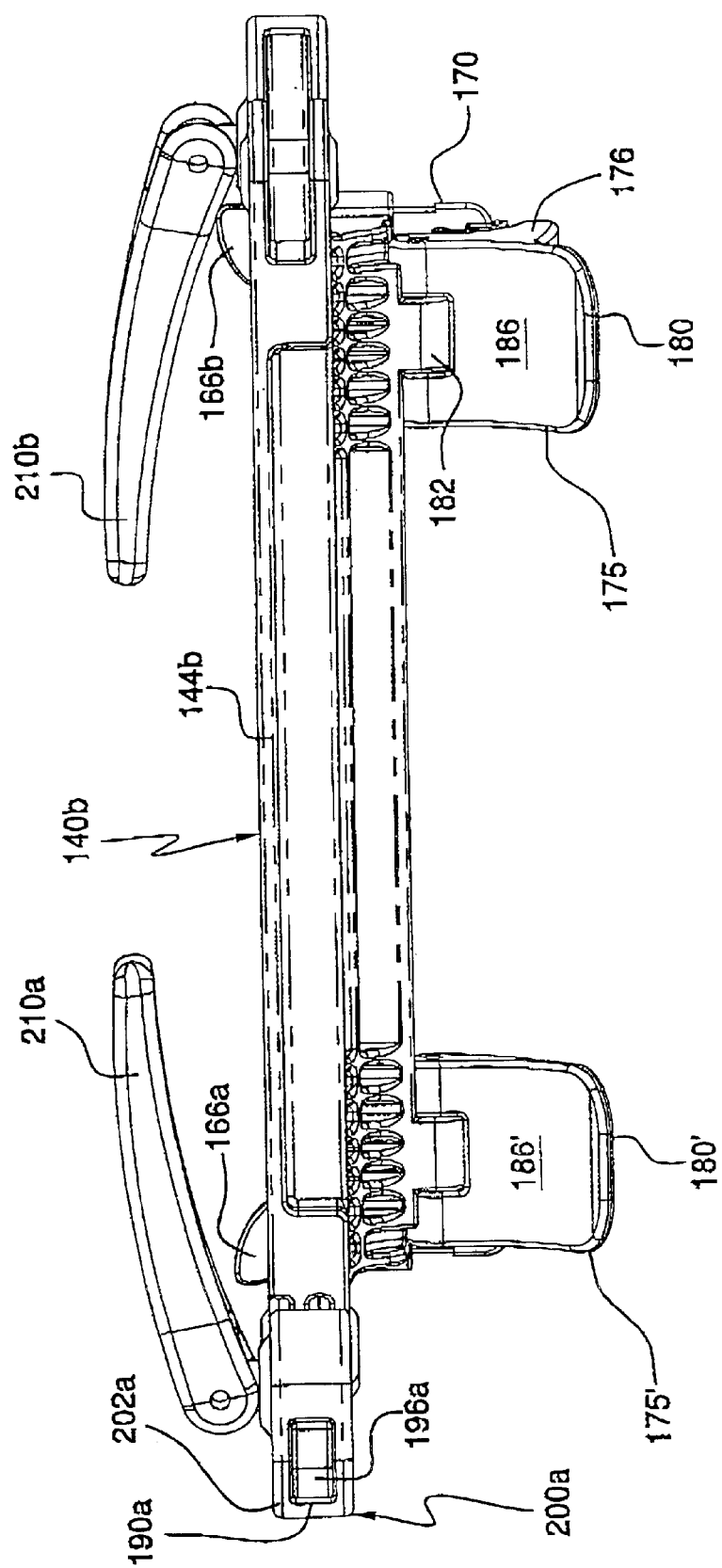
FIG. 27 is a side view of the access device of FIG. 24.

Two other features of the side members 140a and 140b are also worthy of mention. First, the upper edge 44 of the frame 20 shown in FIGS. 1–10 is generally tapered. The side edges 144a and 144b of the first and second side members 140a and 140b in FIGS. 13–27 are shaped a little bit differently, though. In particular, each side edge 144a and 144b is relatively thin and extends generally horizontally outwardly from the rest of the side member 140a and 140b. (This is best seen in FIGS. 16 and 22.) This can make it easier for a physician to physically clamp a light or a surgical tool to the frame 120 during a procedure, providing a convenient mounting mechanism immediately adjacent to the access port 122 without requiring anyone to hold the light or tool manually. Both the suture pad idea and the side edge mounting concept could be incorporated into the previous embodiment and used for the same respective purpose in that design.

The other feature worthy of mention is that each of these side members 140a and 140b includes a suture pad, 145a, 145b, which desirably extends along the side 126, 127 of the access port 122. More specifically, the suture pad 145a is carried by the first side member 140a adjacent the first longitudinal side 126 of the access port 122 while the suture pad 145b is carried by the opposite side member 140b adjacent the second longitudinal side 127 of the access port 122. Conventional retractors move some tissues (e.g., the ribs and associated skin and musculature) out of the way, but the physician has a limited range of options for suturing internal tissues (e.g., the pericardium) out of the way. Some such retractors have separate physical structures (e.g., posts or the like) about which the physician may physically tie the suture. Due to the limited number of such structures, the angle at which this internal suture may be oriented is somewhat limited. Some other retractors have sutures anchored thereto when shipped, but there is no way to reposition the attachment of this suture to the retractor. Consequently, if the physician decides to move the tissue being held by a suture to a different position, the existing suture must be cut and a new one attached.

The suture pads 145a and 145b of FIGS. 13–27 give the physician the ability to suture to the tissue and then suture or re-suture anywhere along the length of the suture pad 145a, 145b to achieve the appropriate retraction. As opposed to current designs which offer a limited number of attachment positions, these suture pads 145a, 145b essentially provide an infinite number of connection locations, enabling a physician to reorient the sutured tissue by moving the suture to a different location on the pad 145a, 145b to alter the direction the suture is pulling. In use, the physician will pass the suture through the patient's tissue and through one of the suture pads 145a or 145b and may tie a knot at each end to hold the suture in place, as is conventional.

To facilitate ease of use, each suture pad 145a, 145b desirably protrudes inwardly from the inner surface (unnumbered) of the associated side member 140a or 140b a sufficient distance to allow easy insertion of the needle through a sufficient thickness of material to withstand the retraction force on the suture by the tissue. The suture pad 145a, 145b is ideally made from a resilient polymer. Ideally, the polymer should be soft enough to be sutured through without undue force, e.g. with a hardness of about 30–65 Shore A hardness. The polymer should also have sufficient strength to resist tearing under the force being applied to the suture even during an extended surgical procedure. Silicone is a likely candidate for the polymer because it is very tear resistant and can be cross-linked to a selected hardness. A second family of materials believed to be appropriate for this application would be a polyurethane or urethane/nylon hybrid. These materials are also tear resistant and can be formulated to yield a range of hardnesses.

The suture pads 145a and 145b can be directly bonded to the associated side member 140a or 140b. This can be done with suitable adhesives, but due to consistency of bond strength and environmental conditions during sterilization, this method generally is not preferred. Instead, the suture pads 145a, 145b may be "over-molded" to the interior face (unnumbered) of the side member 140a, 140b. In conventional over-molding processes, a second material, which must be compatible with the first, is injection molded directly onto the surface. The second molten material, when it is injected, softens the first base material causing a mixing of the two materials at the interface of the two, causing a very strong bond. If the side member 140a, 140b is formed of a polycarbonate resin or the like, urethanes or urethane compounds are currently the material of choice due to their compatibility with polycarbonates.

In the embodiment of FIGS. 1–12, the two wings 40 were effectively rigidly attached to one another by means of the base 54 of the manually graspable tab 50. Optimally, these components are all integrally formed, making manufacture relatively simple and cost-effective. Unfortunately, this simple design effectively precludes one from reshaping the opening of the access port 22 by moving the wings 40, with respect to one another.

In the embodiment of FIGS. 13–27, these rigid, integral connections between the wings 40 are replaced by means of lateral members 190a and 190b. The first lateral member 190a serves to adjustably connect the first end (unnumbered) of the first side member 140a to the first end (unnumbered) of the second side member 140b. At least one of the first ends (unnumbered) of these side members 140a, 140b is movable along the length of the first lateral member 190a to permit adjustment of the space between the first ends (unnumbered) of the side members 140a, 140b.

If so desired, both of the side members 140a, 140b may be adjustably attached to the first lateral member 190a so they may slide along the length thereof. In the illustrated embodiment, though, the first lateral member 190a has a fixed end 194a and a free end 196a. The fixed end 194a is pivotally anchored directly to the first side member 140a by means of a pivot pin 198a. This pivot pin 198a permits the first side member 140a to pivot with respect to the fixed end 194a of the first lateral member 190a, but anchors the first end (unnumbered) of the first side member 140a against lateral movement along the length of the first lateral member 190a.

The first end (unnumbered) of the second side member 140b is slidably attached to the first lateral member 190a and is optimally also pivotable with respect to the first lateral member 190a. This can be achieved in a variety of ways, such as by means of a ball joint carried about a threaded shaft. In the illustrated embodiment, the second side member 140b is attached to the first lateral member 190a by means of a carriage 200a. This carriage 200a has a body 202a having a channel (unnumbered) running along its length within which the first lateral member 190a is slidably received. The first end (unnumbered) of the second side member 140b is attached to the carriage 200a by means of a pivot pin 204a. This pivot pin 204a permits the second side member 140b to pivot with respect to the carriage 200a and the first lateral member 190a, but restricts the first end (unnumbered) of the second side member 140b with respect to the carriage 200a.

Thus, the first end (unnumbered) of the first side member 140a is pivotably anchored to the first lateral member 190a while the second side member 140b is pivotably attached to the first lateral member 190a but is free to slide therealong. As a consequence, movement of the carriage 200a laterally along the first lateral member 190a will move the first ends (unnumbered) of the two side members 140a and 140b with respect to one another. In this manner, the first end (unnumbered) of the access port 122 can be expanded or contracted as the needs of the procedure dictate.

The opposite end of the frame 120 may take much the same configuration, but arranged as a mirror image. Hence, the second end (unnumbered) of the second side member 140b is pivotably anchored to the fixed end 194b of the second lateral member 190b by means of a pivot pin 198b. The second end (unnumbered) of the first side member 140a is pivotably and slidably connected to the second lateral member 190b by means of a carriage 200b and a pivot pin 204b.

In a particularly preferred embodiment, the surgical access device 110 provides a mechanism for increasing the mechanical advantage of a force applied to the carriage 200a or 200b to move it along the lateral member 190a or 190b along which it is carried and a mechanism for locking the carriage 200a, 200b in a desired position with respect to the lateral member 190a, 190b. In the device 110 of FIGS. 13–27, the lateral members 190a, 190b are provided with a series of regularly spaced gear teeth (e.g., teeth 192b on the second lateral member 190b) along much of their length. A gear (not shown) carried by the carriage 200a, 200b may be provided with mating gear teeth and an operator may turn the gear (not shown) by means of a gear handle 210a or 210b attached thereto. Turning of the handle 210a, 210b will move the carriage 200a, 200b laterally along the lateral member 190a, 190b, with the gear (not shown) ratio of the gear and teeth 192b determining the mechanical advantage.

This gear handle 210a, 210b may also be used to releasably lock the carriage 200a, 200b in a desired position. The gear (not shown) is attached to the handle 210a or 210b by means of a locking pin 212a or 212b (respectively). The back surface (unnumbered) of the handle 210a, 210b has a cam surface which is adapted to bear against the body 202a, 202b of the carriage 200a, 200b, lifting the locking pin 212a, 212b when the handle 210a, 210b is pivoted vertically downwardly toward the carriage body 202a, 202b, i.e. in the positions illustrated in FIGS. 13–27. This will pull the gear (not shown) into a relatively tight clamping engagement with the associated lateral member 190a or 190b, restricting motion of the carriage 200a, 200b therealong. Lifting the handle 210a, 210b upwardly (as indicated by the arrows in FIG. 18) into a more vertical position, i.e., wherein the tip of the handle 210a, 210b is moved away from the body 202a, 202b of the carriage 200a, 200b, will release this clamping force, permitting the operator to again move the carriage 200a, 200b along the lateral member 190a, 190b. Preferably, the handle 210a, 210b releases the clamping force shortly after being lifted from the position shown in the drawings rather than requiring the handle 210a, 210b to be fully vertical before the gear (not shown) is free to turn. This will ensure that the handle 210a, 210b still extends radially outwardly from the pin 212a, 212b, making it easier to turn the handle 210a, 210b to advance the carriage 200a, 200b with the gear (not shown). During the initial deployment of the surgical access device 110 in an incision (described more fully below), it is anticipated that the handles 210a, 210b will be positioned in their lower, locked position, limiting movement of the side members 140a and 140b away from one another until the flanges 170, 170', 175 and 175' are properly deployed. Thereafter, one or both of the handles 210a, 210b may be moved upwardly sufficiently to permit the ends (unnumbered) of the side members 140a, 140b to be moved away from one another to reshape the access port 122.

The illustrated design permits the first ends (unnumbered) of the side members 140a and 140b to be moved away from or toward one another along the first lateral member 190a without requiring any movement of the second ends (unnumbered) of the side members 140a, 140b. Alternatively, the second ends (unnumbered) of the side members 140a, 140b can be moved with respect to one another along the second lateral member 190b without requiring any movement of the first ends (unnumbered) of the side members 140a, 140b.

For example, the device 110 may be initially deployed with both carriages 200a, 200b locked against movement with respect to the associated lateral member 190a, 190b and with the side members 140a and 140b positioned immediately adjacent another, as shown in FIGS. 13–18. The handle 210a of the first carriage 200a can be lifted upwardly from the illustrated position and rotated to move the carriage 200a with respect to the first lateral member 190a. The first end (unnumbered) of the first side member 140a will pivot with respect to the fixed end 194a of the first lateral member 190a about pivot pin 198a and the first end (unnumbered) of the second side member 140b will pivot with respect to the carriage 200a about the pivot pin 204a. At the same time, the second end (unnumbered) of the second side member 140b will pivot about the pivot pin 198b and the first side member 140a will pivot with respect to the carriage 200b about the pivot pin 204b. Once the carriage 200a has been moved the desired distance toward the free end 196a of the first lateral member 190a, the handle 210a may again be pushed downwardly toward the illustrated orientation to lock the carriage 200a in place on the lateral member 190a. If this yields an access port 122 of a suitable size and shape, the operator may stop at that point. If it is desired to move the second ends (unnumbered) farther apart to further enlarge and reshape the access port 122, the same procedure can then be repeated to move the second carriage 200b toward the free end 196b of the second lateral member 190b.

In the embodiment of FIGS. 1–12, the device 10 includes a pair of actuators 60, with one actuator 60 being positioned adjacent each end (unnumbered) of the access port 22. Pushing the actuators 60 downwardly serves to urge the flanges 70, 75 away from one another and seat the access port 22 in an opening in the patient's tissue. This works well when the wings 40 of the frame 20 remain fixed with respect to one another, but this same arrangement will not lock both ends of the flanges 70, 75 in a retracting position if the wings 40 were somehow detached from one another and moved apart.

The embodiment of FIGS. 13–27 solves this problem by splitting each of the actuators 160 into separate lateral segments 161a and 161b. In particular, the first lateral segment 161a of each actuator 160 is carried by the first side member 140a and the second lateral segment 161b of each actuator 160 is carried by the second side member 140b. This structure is best seen with reference to FIGS. 16 and 17.

Figure 15:
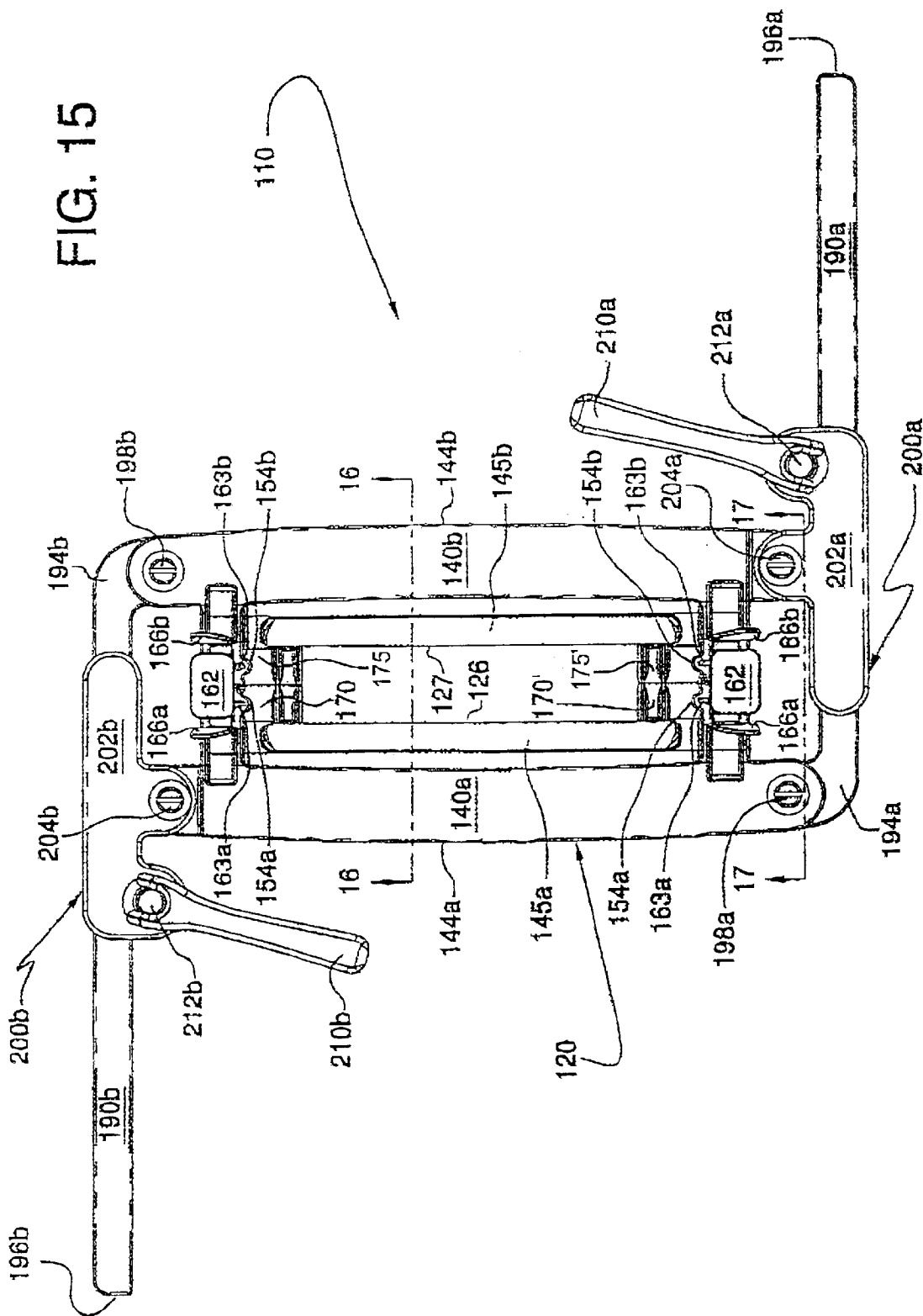
FIG. 15 is a top view of the access device of FIG. 13.
Figure 16:
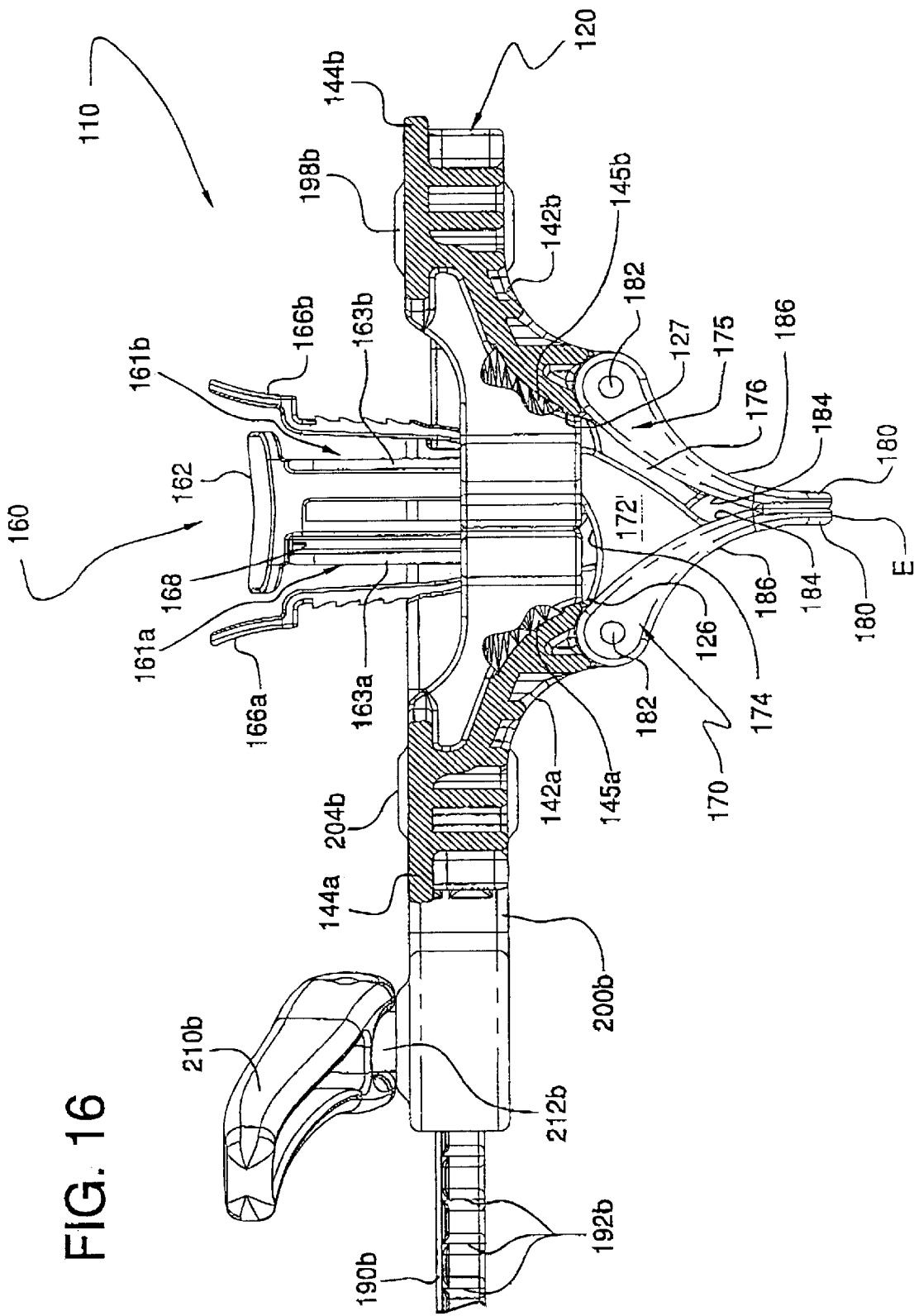
FIG. 16 is a partial cross sectional view taken along line 16—16 of FIG. 15.
Figure 17:
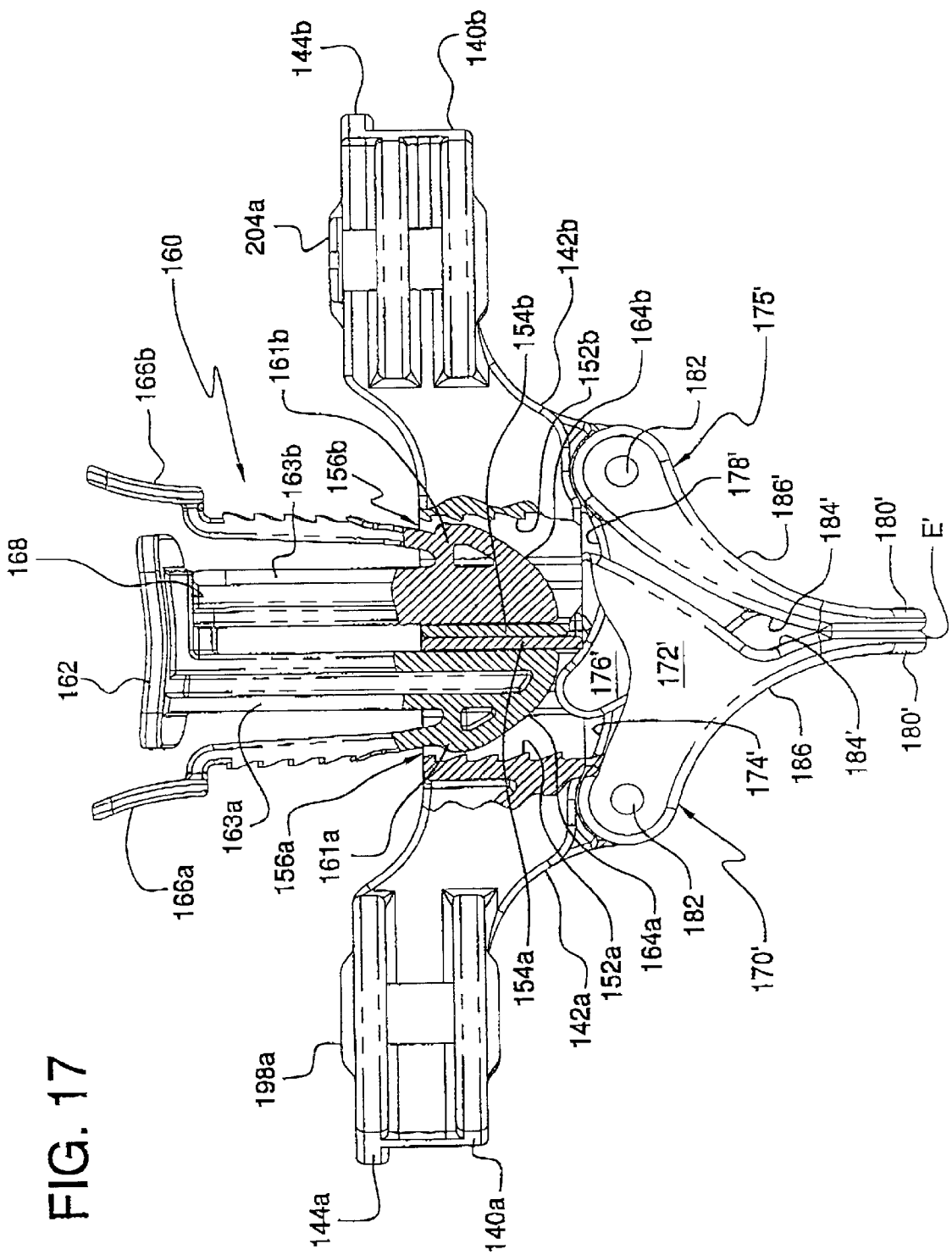
FIG. 17 is a schematic, partially broken-away view taken generally along line 17—17 of FIG. 15.
Figure 18:
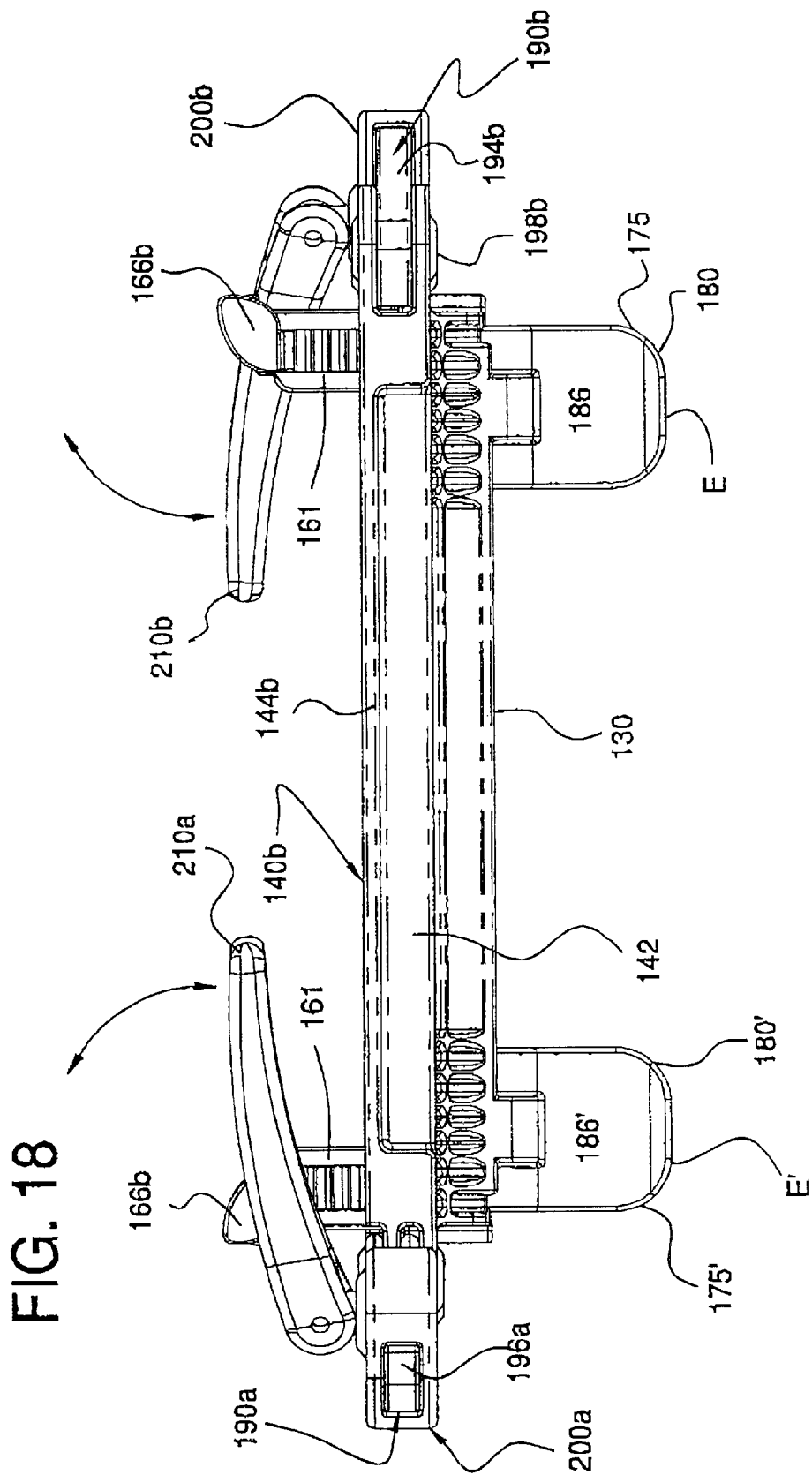
FIG. 18 is a side view of the access device of FIG. 13.
Figure 19:
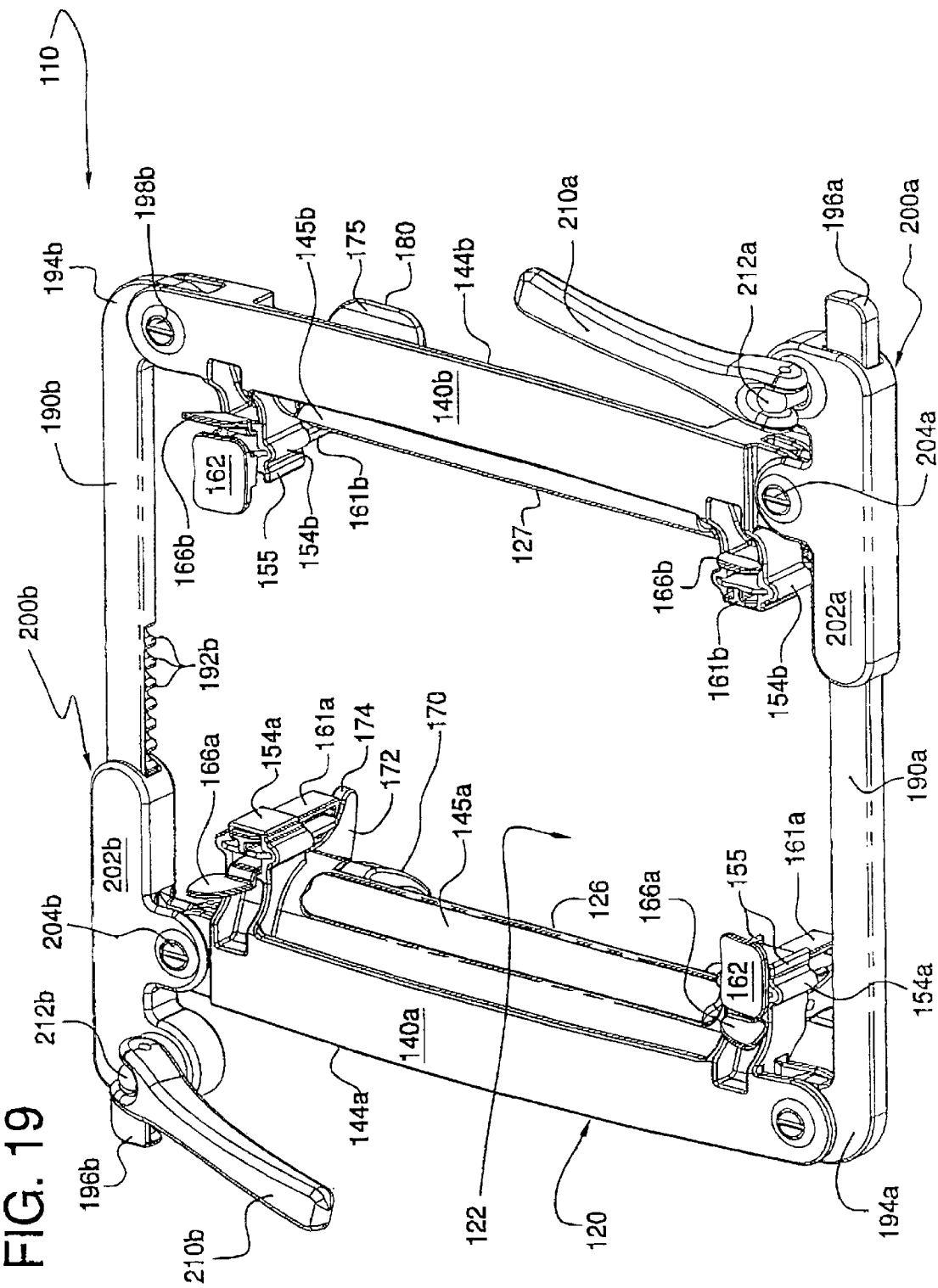
FIG. 19 is a top perspective view of the access device of FIG. 13, but wherein the frame is in a retracting configuration.
Figure 20:
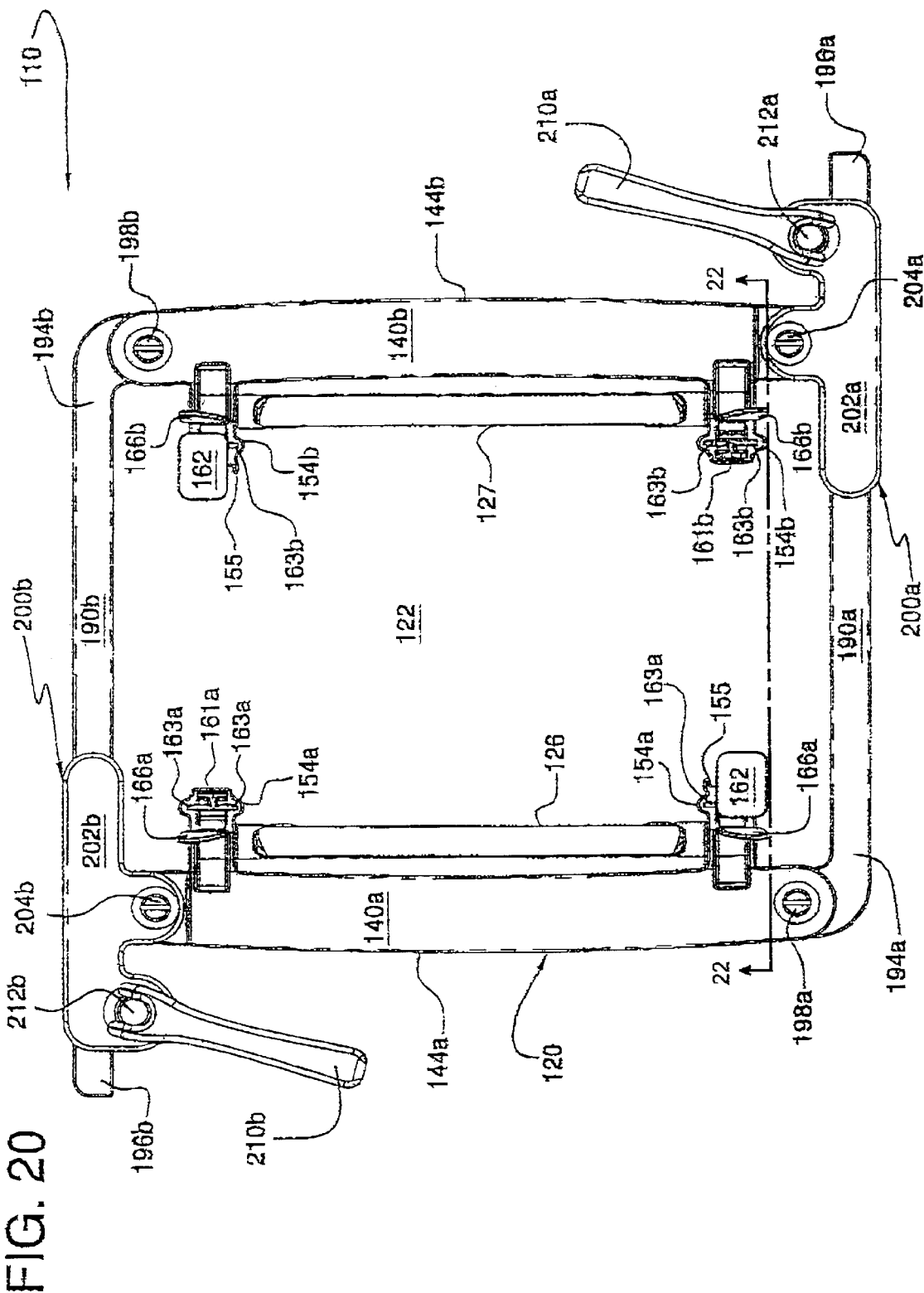
FIG. 20 is a top view of the access device of FIG. 19.
Figure 21:
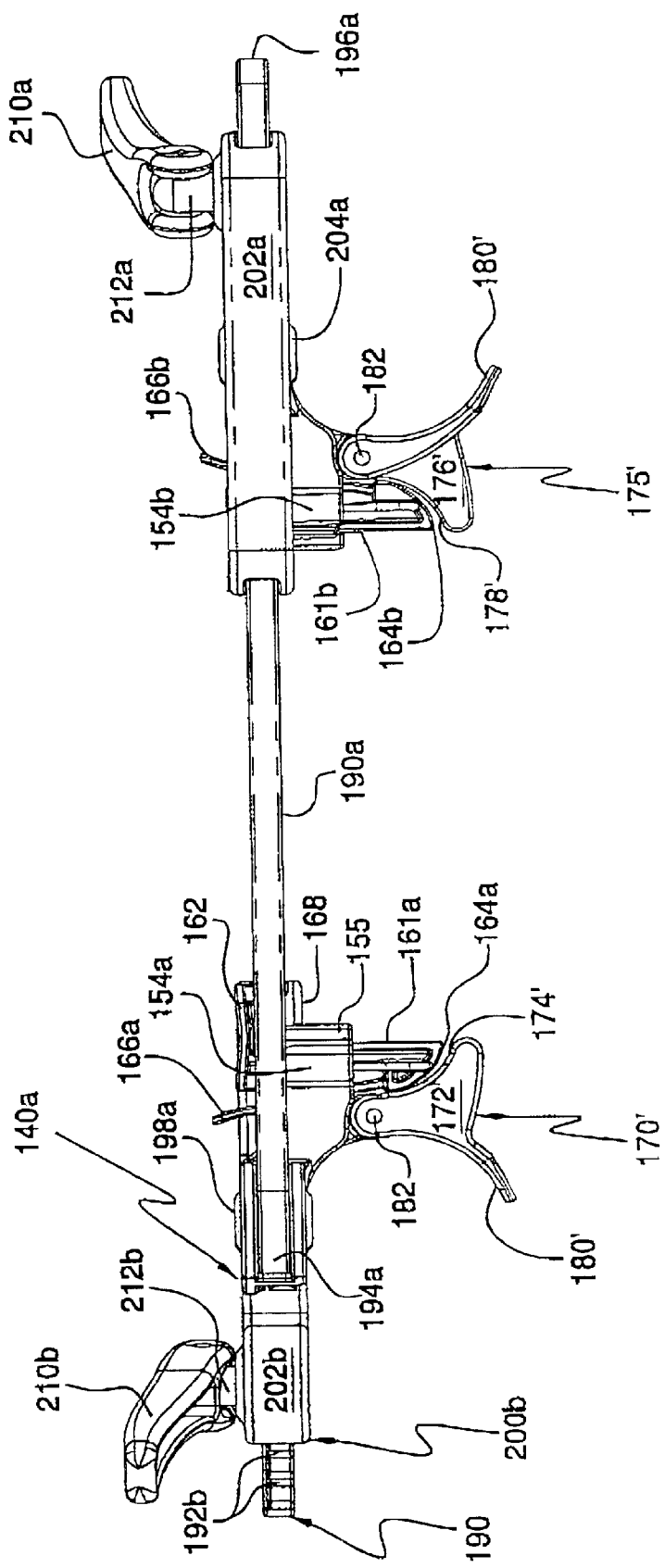
FIG. 21 is an end view of the access device of FIG. 19.

FIG. 16 is a partial cross sectional view taken along line 16—16 of FIG. 15, with a portion of the second lateral member 190b broken away for purposes of this drawing. FIG. 17 schematically illustrates an end view from the perspective of line 17—17 in FIG. 15 if the first lateral member 190a and the first carriage 200a were removed. A portion of each of the actuator guides 154a and 154b have been broken away to better show the structure of the body of the actuator 160.

The first lateral segment 161a of each actuator 160 is received in a channel (156a in FIG. 17) in the first actuator guide 154a. One such first actuator guide 154a may be integrally formed as an inward extension adjacent each end (unnumbered) of the first side member 140a. Similarly, the second lateral segment 161b of each actuator 160 is received in a second actuator guide 154b. One such second actuator guide 154b may be integrally formed as an inward extension adjacent each end of the second side member 140b. When the frame 120 is in its insertion configuration, as shown in FIGS. 16 and 17, the first and second actuator guides 154a and 154b desirably abut one another at each end (unnumbered) of the frame 120, defining a periphery which extends completely about the access port 122. In order to better seat the actuator guides 154a, 154b in such an abutting relationship, one guide of each pair of actuator guides 154a, 154b may be provided with a pair of opposed ears 155 (best seen, perhaps, in FIGS. 19 and 24) which define a shallow, U-shaped channel (unnumbered). This will help direct the other guide 154a, 154b into the proper position such that opposed faces (unnumbered) of the two actuator guides 154a and 154b abut directly against one another, as shown in FIG. 17.

The first lateral segment 161a is slidably received in the first actuator guide 154a. FIGS. 16 and 17 show the actuators 160 in their upper, insertion positions wherein the flanges 170 and 175 (or, in the case of FIG. 17, 170' and 175') are permitted to abut one another in their respective insertion positions. In this position, the first lateral segment 161a extends upwardly above the first actuator channel 156a and is relatively free to move vertically within the channel 156a. Each of the lateral segments 161a, 161b is desirably provided with a generally vertically extending rail 163a or 163b that is received in a track formed in the guide 154a, 154b. As noted above, this will help stabilize the actuator segments 161a, 161b and guide them to move more or less vertically within the channels 156a and 156b with a minimum of shifting about.

When the frame 120 is in its insertion configuration, the first and second lateral segments 161a and 161b are positioned adjacent one another. This permits them to be urged downwardly together as a unit for simultaneous deployment of the flanges 170, 175, 170', 175'. If so desired, an operator can push directly against the tops of both of the lateral segments 161a, 161b with the pad of a single thumb. In the illustrated embodiment, each actuator 160 includes a manually engagable pad 162 which is attached to one of the two lateral segments 161a, 161b, but extends over the top of the other lateral segment 161a, 161b. In FIG. 17 the pad 162 is attached to the first lateral segment 161a while in FIG. 16 the pad 162 is attached to the second lateral segment 161b. The lower surface 168 of this pad 162 is adapted to abut the top of the lateral segment 161a, 161b to which it is not attached, permitting both lateral segments 161a, 161b to be depressed within their respective channels 156a, 156b merely by pushing on a single pad 162.

Each of the lateral segments 161a and 161b is provided with a locking pawl 166a or 166b. This locking pawl 166a, 166b is similar to the locking pawl 66 of the embodiment shown in FIGS. 1–12, but the teeth of the locking pawls 166a and 166b are oriented to face laterally outwardly in a direction away from the other lateral segment 161a, 161b. Each of the actuator channels 156a and 156b is provided with an inner surface 152a or 152b which includes teeth adapted to mate with the teeth on the associated locking pawl 166a, 166b to releasably retain the actuator 160 in a selected retracting position, e.g., the position shown in FIGS. 19–23.

FIGS. 19–23 illustrate one possible retracting configuration of the frame 120 wherein the access port 122 is substantially larger than the access port 122 in the frame's 120 insertion configuration shown in FIGS. 13–18. In this particular retraction configuration, each of the side members 140a and 140b is generally parallel to the other and each of the lateral members 190a and 190b is also generally parallel to the other, defining a parallelogram. In this particular version, the side members 140a, 140b are generally perpendicular to the lateral members 190a, 190b, yielding a frame 120, which is generally rectangular in shape. It is also worth noting that each of the actuators 160 have been split into component parts, with the first lateral segment 161a being carried by the first side member 140a and being spaced from the second lateral segment 161b, which is carried by the second side member 140b.

In moving the frame 120 from the insertion configuration shown in FIGS. 13–18 to the retracting configuration shown in FIGS. 19–23, the first carriage 200a may be moved along the first lateral member 190a and the second carriage 200b may be moved along the second lateral member 190b using the process described above. These two carriages 200a, 200b may be moved simultaneously so that the two side members 140a and 140b remain generally in their original, parallel orientation with respect to one another. Alternatively, they may be moved completely independently from one another. For example, the first ends (unnumbered) of the side members 140a, 140b may be spaced apart from one another to the full extent shown in FIGS. 19–23, only thereafter moving the second ends (unnumbered) of the side members 140a, 140b away from one another along the second lateral member 190b.

FIGS. 24–27 show a different retracting configuration of the frame 120. The first ends (unnumbered) of the side members 140a and 140b have been moved away from one another along the length of the first lateral member 190a about the same distance as that necessary to reach the configuration shown in FIGS. 19–23. However, the second ends (unnumbered) of the side members 140a, 140b have not been moved so far apart. As a consequence, the frame 120 is no longer generally rectangular in shape, but has instead taken on the shape of an isosceles trapezoid, with the two side members 140a and 140b no longer remaining in their original, generally parallel orientation. It is believed that in most circumstances encountered in normal use of the device 110, the two lateral members 190a, 190b will remain generally parallel to one another due to the self-centering capabilities provided by the flanges 170, 175 and 170', 175'. The fact that each side member 140a and 140b is pivotably attached to each lateral member 190a and 190b permits a complete freedom to shape the access port 122 as desired, though, and this surgical access device 110 is flexible enough to define virtually any shape that has two sides of about the same length.

Since the surgical access device 10 or 110 will be in direct contact with the patient's tissue, it should be formed of a biocompatible material. The specific material chosen will depend on a number of factors, including the anticipated mechanical stresses on the parts during use, whether it will be discarded after a single use or, less likely, will be sterilized and reused on different patients, etc. In order to minimize manufacturing costs if the devices 10, 110 are intended to be disposable; all of the parts can optimally be formed of an injection moldable plastic material, such as a biocompatible organic resin or thermoplastic material. Given the present teaching, the selection of an appropriate material for a given clinical application should be well within the capabilities of a skilled designer.

As noted above, the present invention also contemplates a method of gaining surgical access to a body cavity. In the following discussion, reference is made to the embodiments of the invention illustrated in FIGS. 1–12. It is to be understood, however, that these figures are used solely for convenience and that the present method can be utilized with devices 10, 110, which differ significantly from the embodiments illustrated in the drawings so long as they serve the functions called for in the method.

In accordance with this method, the operator is presented with a surgical implant, e.g., the surgical access device 10 illustrated in FIGS. 1–12. The physician cuts an elongate, generally linear incision through the patient's tissue. This incision should be at least as long as the leading edge E of the surgical access device 10. If so desired, one can minimize the length of this incision to be substantially the same as the length of the leading edge E of the device 10. It would be advisable to make such an incision generally I-shaped, however, with a pair of shorter transverse incisions at each end of the longer main incision. This will define a pair of tissue flaps which can be spread apart by the flanges 70, 75. If such short transverse incisions are not made, the physician would risk tearing the tissue when the flanges 70, 75 are moved from their insertion position to a retraction position.

The incision can pass through the entire thickness of the patient's tissue, including both cutaneous and subcutaneous layers. In one preferred method, though, the physician will first separate the cutaneous tissue from the subcutaneous tissue. The cutaneous tissue can be pulled back, and the incision can be made in the exposed subcutaneous tissue. This is particularly desirable when one is using the surgical access device 10 to gain access to the patient's thoracic cavity through the intercostal space between adjacent ribs.

Once a suitable incision has been made through the patient's tissue, the leading edge E of the surgical access device 10 can be inserted into the incision. The surgeon will typically urge a length of each of the first and second flanges 70, 75 through the incision by pushing downwardly on the frame 20. Preferably, the flanges 70, 75 are inserted far enough through the incision to position the leading edges 80 of the flanges 70, 75 below the inner surface of the tissue, i.e., the tissue surface that faces the body cavity.

Once the flanges 70, 75 have been properly inserted into and extend through the incision, the physician can urge the flanges 70, 75 laterally away from one another. In the illustrated embodiment of the surgical access device 10, the physician need only move the actuators 60 downwardly within the actuator channels 56 of the manually graspable tabs 50. This can be facilitated by placing one finger of each hand beneath the manually graspable tab 50 at either end of the frame 20. The operator can then press down on the actuator 60 by pushing the pad 62 of the actuator 60 with a thumb, using the manually graspable tab 50 to provide leverage.

As the actuators 60 are pushed down and urge the flanges 70, 75 away from one another, the flanges 70, 75 will expand the opening through the patient's tissue initially defined by the incision. Since the actuators 60 will deploy the flanges 70, 75 at the same rate, the device 10 inherently tends to center the access port 22 laterally within the expanded opening.

As noted above, the leading edges 80 of the flanges 70, 75 are desirably positioned below the inner surface of the tissue. When the flanges 70, 75 are moved from their insertion position (FIGS. 1–5) laterally away from one another toward a retracting position, the leading edges 80 of the flanges 70, 75 will tend to grasp the lower surface of the tissue. Once the incision has been widened enough to permit any reasonable access, the flanges 70, 75 have reached a first retracting position, and the operator may simply stop. Desirably, the mating ratchet fittings on the actuator 60 and manually graspable tab 50 are designed to engage one another to lock the flange 70, 75 in such a position.

More preferably, though, the operator will not stop at the first narrow opening but instead will continue to move the flanges 70, 75 through a wider range of retracting positions until the frame 20 is suitably seated in the tissue. When the operator continues to move the flanges 70, 75 away from one another, the outer surfaces 86 of the flanges 70, 75 will act upwardly against the lower surface of the tissue with increasing force. This will draw the frame 20 downwardly with respect to the tissue, helping seat the frame 20 in the tissue. Desirably, the operator will continue urging the flanges 70, 75 away from one another until the access port 22 is positioned below the upper surface of the tissue in which the incision was initially made. In this position, the tissue is retained between the outer surface 86 of each flange 70, 75 and the concave outer surface 42 of the adjacent wing 40. This will rather securely position the access port 22, enabling an operator to reliably move medical instruments through the access port 22 into the body cavity without fear of inadvertently moving or dislodging the surgical access device 10.

There are numerous advantages to the present invention over prior art retractors or access ports. Among these advantages are the self-seating characteristics of the surgical access device 10 and the improved accessibility of the body cavity attained in this fashion.

Prior art retractors simply provide a means for spreading the margins of an incision away from one another. Such retractors typically cannot engage the tissue and hold themselves in place. As a result, the physician must rely on friction between the tissue and the retractor to keep the retractor in place. The surgical access device 10 of the present invention, however, provides a much more secure connection between the retractor and the tissue being retracted.

The wings 40 of the access device 10 perform a couple of functions, which significantly enhance the physician's easy access to the body cavity through the access port 22. First, the tissue is retained between the flanges 70, 75 and the adjacent wings 40, helping seat the device 10 in the desired position. The wings 40 will also tend to keep both the subcutaneous tissue and any loose cutaneous tissue away from the open access port 22. In a preferred embodiment, the wings 40 desirably extend at least about 10 mm above the upper surface (unnumbered) of the access port 22. If so desired, the upper edge 44 of each of the wings 40 can extend further upwardly or be specifically shaped to better retain the cutaneous tissue away from the opening.

The surgical access device 10 also provides superior access to the body cavity. This is attributable, at least in part, to the action of the flanges 70, 75 against the under side of the tissue. First, pulling the access port 22 downwardly toward the bottom of the tissue will increase the physician's range of motion laterally within the body cavity. In addition, the flanges 70, 75 will help lift the tissue upwardly on either side of the access port 22. This will also enhance the ability of the physician to gain access to structures positioned laterally with respect to the site of the incision. This is in direct contrast to devices such as the surgical cannula proposed by Garrison et al. in U.S. Pat. No. 5,613,937, discussed above. This long surgical cannula significantly restricts the range of angles through which the medical devices passed through the cannula can be maneuvered.

The physician can remove the surgical access device 10 by retracting the locking pawls 66 of each of the actuators 60. The physician can then raise the actuators 60 upwardly, permitting the flanges 70, 75 to move back toward their insertion position (FIGS. 1–5). This will permit the surgical access device 10 to be removed from the patient and the tissue can simply be stitched back together.

Initial deployment and final extraction of the surgical access device 110 of FIGS. 13–27 may be similar to that of the surgical access device 10. However, the surgical access device 110 of the second embodiment allows more flexibility in shaping the opening through the patient's tissue. As noted previously, it is contemplated that the carriages 200a and 200b will be locked against movement along the respective lateral member 190a or 190b when the frame 120 is in its initial insertion configuration (see, e.g., FIGS. 13–18). After the incision is made through the patient's tissue, the flanges 170, 175, 170', 175' may be inserted simultaneously through the incision. The alignment of the two leading edges E and E' defined by the two pairs of flanges 170, 175, 170', 175' greatly facilitates this simultaneous insertion, but likely is not necessary.

Once the flanges 170, 175, 170', 175' are inserted into the incision, the paired flanges 170, 175, 170', 175' may be urged laterally away from one another into respective retracting positions by pushing downwardly on the actuators 160. If so desired, this may be done in two separate steps, with one actuator 160 being depressed to urge one pair of flanges (e.g., flanges 170 and 175) into their retracting positions and only then depressing the other actuator 160 to urge the other pair of flanges (e.g., flanges 170' and 175') into their retracting positions. It should also be noted that there is no need to urge both pairs of flanges 170, 175, 170', 175' the same distance from their paired flange 170, 175, 170', 175'. As a matter of fact, if the tissue is thicker adjacent one pair of flanges 170, 175, 170', 175' than adjacent the other, it is likely that the flanges 170, 175, 170', 175' adjacent the thinner tissue will be urged farther from one another than will be the flanges 170, 175, 170', 175' adjacent the thicker tissue. Either way, the deployment of the flanges 170, 175, 170', 175' in pairs will tend to simultaneously expand the opening through the patient's tissue and center the access port 122 laterally with respect to the opening.

Before, during or, more preferably, after the deployment of the flanges 170, 175, 170', 175' from their insertion positions to their desired retracting positions, the two side members 140a and 140b may be moved away from one another. As outlined above, this can be accomplished by unlocking the carriages 200a and 200b and moving them laterally along the respective lateral members 190a and 190b. Initially, at least the first ends (unnumbered) of the first and second members 190a, 190b away from one another by moving the first carriage 200a along the first lateral member 190a. If the operator feels that this yields sufficient access to the body cavity of interest, there would be no need to move the second ends (unnumbered) away from one another and the frame 120 can be left in this configuration. If a larger or more nearly rectangular opening were desired, the operator could move the second carriage 200b along the second lateral member 190b to space the second ends (unnumbered) away from one another, as well. Again, the movement of the first ends (unnumbered) away from one another may take place simultaneously with the movement of the second ends (unnumbered) away from one another. Unless a mechanism were employed to ensure that both carriages 200a, 200b moved the same distance along their respective lateral members 190a, 190b, though, the movements of the two pairs of ends (unnumbered) will take place essentially completely independently, even if they take place simultaneously.

Upon completion of the procedure, the frame 120 can be removed by moving the side members 140a and 140b back toward the frame's 120 insertion configuration and moving the actuators 160 upwardly to let the flanges 170, 175, 170', 175' return toward their respective insertion positions. This allows the flanges 170, 175, 170', 175' to be lifted from the opening so the physician may suture the incision closed.

While a preferred embodiment of the present invention has been described, it should be understood that various changes, adaptations, and modifications may be made therein without departing from the spirit of the invention and the scope of the appended claims.

What is claimed is:

1. A surgical device for accessing a body cavity, comprising:
   (a) first and second opposed side members, each of said side members having first and second ends and carrying a downwardly depending flange wherein each flange is pivotable between an insertion position and at least one retracting position;
   (b) a first lateral member adjustably connecting the first end of the first side member to the first end of the second side member, at least one of said first ends being moveable along a length of the first lateral member, thereby permitting adjustment of the space between said first ends;
   (c) a second lateral member adjustably connecting the second end of the first side member to the second end of the second side member, at least one of said second ends being moveable along a length of the second lateral member, thereby permitting adjustment of the space between said second ends; and
   (d) an actuator adapted to engage a deployment surface of each of the flanges to permit an operator to urge the flanges from their respective insertion positions to their respective retracting positions.

2. The surgical access device of claim 1 wherein the actuator is divided into a first lateral segment carried by the first side member and a second lateral segment carried by the second side member.

3. The surgical access device of claim 2 wherein the surgical device has an insertion configuration wherein the first and second lateral segments of the actuator are positioned adjacent one another to permit them to be urged downwardly together as a unit for simultaneous deployment of the flanges.

4. The surgical access device of claim 1 wherein each side member carries at least two spaced-apart flanges, the flanges being arranged to define opposed pairs of flanges.

5. The surgical access device of claim 4 further comprising at least two of said actuators, each opposed pair of flanges being associated with a separate actuator.

6. A surgical device for accessing a body cavity, comprising:
   (a) longitudinally extending first and second opposed side members, each of said side members having first and second ends and carrying a downwardly depending flange;
   (b) a first laterally extending member adjustably connecting the first end of the first side member to the first end of the second side member, at least one of said first ends being moveable along a length of the first lateral member, thereby permitting adjustment of the space between said first ends; and
   (c) a second laterally extending member adjustably connecting the second end of the first side member to the second end of the second side member, at least one of said second ends being moveable along a length of the second lateral member, thereby permitting adjustment of the space between said second ends;
   (d) wherein the first end of the first side member is pivotably anchored in a transverse direction to the first lateral member and the second end of the second side member is pivotably anchored in the transverse direction to the second lateral member.

7. The surgical access device of claim 6 wherein the first end of the second side member is moveable along said length of the first lateral member and the second end of the first side member is moveable along said length of the second lateral member.

8. A surgical device for accessing a body cavity, comprising:
   (a) longitudinally extending first and second opposed side members, each of said side members having first and second ends and carrying a downwardly depending flange;
   (b) a first laterally extending member adjustably connecting the first end of the first side member to the first end of the second side member, at least one of said first ends being moveable along a length of the first lateral member, thereby permitting adjustment of the space between said first ends; and
   (c) a second laterally extending member adjustably connecting the second end of the first side member to the second end of the second side member, at least one of said second ends being moveable along a length of the second lateral member, thereby permitting adjustment of the space between said second ends;
   (d) wherein the first ends of each of the first and second side members are pivotably connected in a transverse direction to the first lateral member and the second ends of each of the first and second side members are pivotably connected in the transverse direction to the second lateral member.

9. The surgical access device of claim 8 wherein the first end of the first side member is pivotably anchored to the first lateral member such that it may not slide laterally therealong and the second end of the second side member is pivotably anchored to the second lateral member such that it may not slide laterally therealong.

10. A surgical device for accessing a body cavity, comprising:
   a) a frame comprising separable first and second side members, the frame having an insertion configuration and at least one retracting configuration;
   b) at least one flange carried by the first side member, said flange being moveable between an insertion position and at least one retracting position;

c) at least one flange carried by the second side member, said flange being moveable between an insertion position and at least one retracting position;

d) at least one actuator having first and second lateral segments, the first lateral segment being carried by the first side member and having a control surface adapted to engage a deployment surface of the flange of the first side member, the second lateral segment being carried by the second side member and having a control surface adapted to engage a deployment surface of the flange of the second side member, the first and second lateral segments of the actuator being positioned adjacent one another when the frame is in its insertion configuration, permitting the lateral segments to be urged downwardly together as a unit for simultaneous deployment of the flanges, the first and second lateral segments of the actuator being spaced from one another when the frame is in its retracting configuration.

11. The surgical access device of claim 10 wherein the actuator has an insertion position and at least one retracting position, the flanges being moveable into their respective insertion positions when the actuator is in its insertion position, but the actuator in said at least one retracting position biasing each flange into a respective retracting position.

12. The surgical access device of claim 11 wherein a locking face of the first lateral segment and a mating locking face of the first side member engage one another to limit movement of the flange carried by the first side member toward its insertion position when an operator lets go of the actuator.

13. The surgical access device of claim 12 wherein a locking face of the second lateral segment of a mating locking face of the second side member engage one another to limit movement of the flange carried by the second side member toward its insertion position when an operator lets go of the actuator.

14. A method of gaining surgical access to a body cavity, comprising:

(a) providing a surgical implant comprising a frame having first and second opposed side members, each of said side members having first and second ends and carrying a downwardly depending flange; a first lateral member adjustably connecting the first end of the first side member to the first end of the second side member; and a second lateral member adjustably connecting the second end of the first side member to the second end of the second side member;

(b) making an incision through the patient's tissue to define an opening therethrough;

(c) simultaneously inserting the flanges of the first and second side members through the incision;

(d) thereafter, urging the first and second flanges laterally away from one another, thereby simultaneously expanding the opening through the patient's tissue and centering the access port laterally within the opening;

(e) moving at least one of the first end of the first side member and the first end of the second side member along a length of the first lateral member to move said first ends away from one another; and (f) moving at least one of the second ends of the first and second side members along a length of the second lateral member to move said second ends away from one another;

(g) wherein the first ends are moved away from one another independently of the movement of the second ends away from one another.

15. The method of claim 14 wherein during insertion of the flanges through the incision the first ends are positioned adjacent one another and the second ends positioned adjacent one another, but movement of the first ends away from one another spaces the first ends from one another without moving the second ends away from one another.

16. The method of claim 14 wherein during insertion of the flanges through the incision the first and second side members have a first orientation with respect to one another, movement of the first ends away from one another changing the orientation of the first and second side members with respect to one another to a second, different orientation.

17. The method of claim 16 wherein the first and second side members are generally parallel to one another in the first orientation, but the first ends are moved with respect to one another without a corresponding movement of the second ends with respect to one another such that the first and second side members are not parallel to one another in the second orientation.

18. A surgical access device, comprising:

(a) a frame defining an access port having opposed first and second sides;

(b) a first flange carried on the frame, which extends along the first side of the access port and is pivotable between a rest position and at least one retracting position;

(c) a second flange carried on the frame which extends along the second side of the access port and is pivotable between a rest position and at least one retracting position; and (d) at least one actuator configured and arranged for simultaneously urging both the first flange and the second flange from the rest position to the at least one retracting position upon actuation of the actuator.

19. The surgical access device of claim 18 wherein the access device is supportively connected to a second surgical device.

20. A surgical access device, comprising:

(a) a frame;

(b) a pair of transversely spaced flanges carried on the frame, including at least:

(i) a first flange having a longitudinally elongate leading edge which is pivotable between a rest position and at least one retracting position, and (ii) a second flange having a longitudinally elongate leading edges which is pivotable between a rest position and at least one retracting position, and (c) at least one actuator configured and arranged for simultaneously urging both the first flange and the second flange from the rest position to the at least one retracting position upon actuation of the actuator;

(d) wherein pivoting of the first and second flanges from the rest position to the retraction position upon actuation of the actuator causes the leading edges of the first and second flanges to transversely move away from one another.

21. The surgical access device of claim 20 wherein the access device is supportively connected to a second surgical device.

* * * * *

UNITED STATES PATENT AND TRADEMARK OFFICE
CERTIFICATE OF CORRECTION

PATENT NO. : 6,746,396 B1
DATED : June 8, 2004
INVENTOR(S) : Segermark et al.

It is certified that error appears in the above-identified patent and that said Letters Patent is hereby corrected as shown below:

Column 1,
Line 5, "Int'" should read -- Int'l --;
Line 7, "Engligh" should read -- English --

Column 23,
Line 34, "of a" should read -- and a --

Signed and Sealed this

Eighth Day of March, 2005

JON W. DUDAS
*Director of the United States Patent and Trademark Office*